US006506415B2

(12) United States Patent
Baserga et al.

(10) Patent No.: US 6,506,415 B2
(45) Date of Patent: *Jan. 14, 2003

(54) METHOD OF INDUCING RESISTANCE TO TUMOR GROWTH

(75) Inventors: Renato Baserga, Ardmore, PA (US); David Abraham, Wynnewood, PA (US); Mariana Resnicoff, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/832,382

(22) Filed: Apr. 11, 2001

(65) Prior Publication Data

US 2001/0022977 A1 Sep. 20, 2001

Related U.S. Application Data

(63) Continuation of application No. 08/864,641, filed on May 29, 1997, now Pat. No. 6,312,684, which is a continuation-in-part of application No. 08/340,732, filed on Nov. 16, 1994, now Pat. No. 5,714,170, and a continuation-in-part of application No. PCT/US95/14952, filed on Nov. 15, 1995.

(51) Int. Cl.$^7$ .......................... A61K 35/12; A61F 13/00; A61F 2/00; C12N 5/02; C07H 21/04
(52) U.S. Cl. ........................ 424/573; 424/572; 424/422; 424/424; 424/93.2; 424/93.21; 435/320.1; 435/325; 536/23.1; 514/44; 530/300; 530/350
(58) Field of Search ........................ 435/325, 320.1; 530/350, 300; 536/23.1; 514/44, 2; 424/93.2, 93.21, 572, 573, 422, 424

(56) References Cited

U.S. PATENT DOCUMENTS

| | | | |
|---|---|---|---|
| 4,736,866 A | 4/1988 | Leder et al. | 800/1 |
| 4,873,191 A | 10/1989 | Wagner et al. | 435/172.3 |
| 5,077,059 A | 12/1991 | Mishima et al. | 424/573 |
| 5,139,941 A | 8/1992 | Muzyczka et al. | 435/172.3 |
| 5,173,414 A | 12/1992 | Lebkowski et al. | 435/172.3 |
| 5,252,479 A | 10/1993 | Srivastava | 435/235.1 |
| 5,262,308 A | 11/1993 | Baserga | 435/69.1 |
| 5,272,082 A | 12/1993 | Santoli et al. | 435/240.2 |
| 5,354,674 A | 10/1994 | Hodgson | 435/172.3 |
| 5,354,678 A | 10/1994 | Lebkowski et al. | 435/172.3 |
| 5,399,346 A | 3/1995 | Anderson et al. | 424/93.21 |
| 5,460,831 A | 10/1995 | Kossovsky et al. | 424/493 |
| 5,714,170 A | * 2/1998 | Baserga et al. | 424/573 |

FOREIGN PATENT DOCUMENTS

| | | |
|---|---|---|
| WO | WO 91/17253 | 11/1991 |
| WO | WO 92/22486 | 10/1994 |
| WO | WO 97/37010 | 10/1997 |
| WO | WO 99/23259 | 5/1999 |

OTHER PUBLICATIONS

Branch; A good antisense molecule is hard to find, 1998, Tibs 23: 45–50.*

Branch; Antisense Drug Discovery: Can Cell–Free Screens Speed the Process?, 1998, Antisense & Nucleic Acid Drug Development 8: 249–254.*

Sell et al., "Simian virus 40 large tumor antigen is unable to transform mouse embryonic fibroblasts lacking type 1 insulin–like growth factor receptor", *Proc. Natl. Acad. Sci. USA*, 1993, 90, 11217–11221.

Sell et al., "Effect of a Null Mutationof the Insulin–Like Growth Factor I Receptor Gene on Growth and Transformation of Mouse Embryo Fibroblasts", *Mol. Cell. Biol.*, 1994, 14, 3604–3612.

Valentinis et al., "The role of the insulin–like growth factor I receptor in the transformation by simian virus 40 T antigen", *Oncogene*, 1994, 9, 825–831.

Coppola et al., A Functional Insulin–Like Growth Factor I Receptor is Required for the Mitogenic and Transforming Activities of the Epidermal Growth Factor.

Resincoff et al., "Rat Glioblastoma Cells Expressing an Antisense RNA to the Insulin–like Growth Factor–1 (IGF–1) Receptor are Nontumorigenic and Induce Regression o Wild–Type Tumors", *Cancer Res.*, 1994, 54, 2218–2222.

Resincoff, M., et al., "Growth Inhibition of Human Melanoma Cells in Nude Mice by Antisense Strategies to the Type 1 Insulin–like Growth Factor Receptor", *Cancer Res.*, 1994, 54, 4848–4850.

Harrington et al., "c–Myc–induced apoptosis in fibroblasts is inhibited by specific cytokines", *EMBO J.*, 1994, 13, 3286–3295.

Goldring and Goldring, "Cytokines and Cell Growth Control", *Crit. Rev. Eukaryot. Gene Expr.*, 1991, 1, 301–326.

Baserga and Rubin, "Cell Cycle and Growth Control", *Crit. Rev. Eukaryot. Gene Expr.*, 1993, 3, 47–61.

(List continued on next page.)

*Primary Examiner*—Anne M. Wehbé
(74) *Attorney, Agent, or Firm*—Woodcock Washburn LLP

(57) ABSTRACT

A method of inducing resistance to tumor growth comprising placing tumor cells in culture in vitro supplemented with a pro-apoptotic agent for a period of time, transferring the tumor cells into a diffusion chamber, thereby producing a cell-containing chamber, inserting the chamber into a mammal for a therapeutically effective time, thereby inducing resistance to tumor growth. The pro-apoptotic agents include nucleic acid molecules, proteins or peptides, non-proteins or non-polynucleotide compounds, and a physical conditions.

12 Claims, 10 Drawing Sheets

OTHER PUBLICATIONS

Pietrzkowski et al., "Constitutive Expression of Insulin–like Growth Factor 1 and Insulin–like Growth Factor 1 Receptro Abrogates All Requirements for Exogenous Growth Factors", *Cell Growth & Diff*, 1992, 3, 199–205.

Pietrzkowski et al., "Roles of Insulinlike Growth Factor 1 (IGF–1) and the IGF–1 Receptor in Epidermal Growth Factor–Stimulated Growth of 3T3 Cells", *Mol. Cell. Biol.*, 1992, 12, 3883–3889.

Buttyan, R., et al., "Induction of the TRPM–2 Gene in Cells Undergoing Programmed Death", *Mol. Cell Biol.*, 1989, 9, 3473–3481.

Kaufman, S.H., "Induction of Endonucleolytic DNA Cleavage in Human Acute Myelogenous Leukemia Cells by Etoposide, Camptothecin, and Other Cytotoxic Anticancer Drugs: A Cautionary Note", *Cancer Res.*, 1989, 49, 5879–5878.

Barry, M.A., et al., "Activation of Programmed Cell Death by Cisplatin, Other Anticancer Drugs, Toxins and Byperthermia", *Biochem Pharmacol*, 1990, 40, 2353–2362.

Bursch, W., et al., "Determination of the length of the histological stages of apoptosis in normal liver and in altered hepatic foci of rats", *Carcinogenesis*, 1990, 11, 847–853.

Lange et al., "IL–4–and IL–5–Dependent Protective Immunity to Onchocerca Volvulus infectie Larvae in BALB/cBYJ mice", *J. Immunol.*, 1994, 153, 205–211.

Lanza et al., "Xenogeneic Humoral Response to Islets Transplated in Biohybrid Diffusion Chambers", *Transplantation*, 1994, 57, 1371–1375.

Trojan et al., "Treatment and Prevention of Rat Glioblastoma by Immunogenic C6 Cells Expressing Antisense Insulin–Like Growth Factor I RNA", *Science*, 1993, 259, 94–97.

Martin et al., "Development of an in Vitro Assay for the Survival of Cells Suspended from BA1112 Rat Sarcomas", *Eur. J. Cancer Clin. Oncol.*, 1983, 19, 791–797.

Preston et al., "Regulation of Apoptosis by Low Serum in Cells of Different Stages of Neoplastic Progression", *Cancer Res.*, 1994, 54, 4214–4223.

Brown, "Gene Therapy 'Oversold' By Researchers, Jounalists", *Washington Post*, Dec. 8, 1995, pp. 1 and A22.

Conley, "Transplantation of nervous system tumors in diffusion chambers", *J. Neurosurg.*, 1974, 41, 332–338.

Kolata, "In the rush toward gene therapy, some see a high risk of failure", *The New York Times*, Jul. 25, 1995, p. C3.

Marshall, "Gene Therapy's Growing Pains," *Science*, 1995, 269, 1050–1055.

Miller, et al., "Gene Gransfer and Antisense Nucleic Acid Techniques," *Parasitology Today*, 1994, 10(3), 92–97.

Tseng, et al., "Antisense oligonucleotide technology in the development of cancer therapeutics," *Cancer Gene Therapy*, 1994, 1(1), 65–71.

Wu–Pong, "Oligonucleotides: Opportunities for Drug Therapy and Research," *Pharm. Tech.*, 1994, 102, 104, 106, 108, 110–112, and 114.

Ray et al., "Ca2+ antagonists inhibit DNA fragmentation and toxic cell death induced by acetaminophen", *FASEB J.*, 1993, 7, 453–463.

Becker et al., "Proliferation of human malignant melanomas is inhibited by antisense oligodeoxynucleotides targeted against basic fibroblast growth factor", *EMBO J.*, 1992, 8(12), 3685–3691.

Abraham, et al., "Survival and Development of larval *Onchocerca volvulus* in Diffusion Chambers Implanted in Primate and Rodent Hosts", *J. Parasitol.*, 1993, 79, 571–582.

Baserga, R., "Oncogenes and the Strategy of Growth Factors", *Cell*, 1994, 79, 927–930.

Scher, C.D., et al., "Platelet–Derived Growth Factor and the Regulation of the Mammalian Fibroblast Cell Cycle", *Biochem. Biophys. Acta.*, 1979, 560, 217–241.

Stiles, C.D., et al., "Dual control of cell growth by somatomedins and platelet–derived growth factor", *Proc. Natl. Acad. Sci. USA*, 1979, 76, 1279–1283.

Ullrich, A. et al., "Insulin–Like Growth Factor I Receptor Primary Structure: Comparison with Insulin Receptor Suggests Structural Determinants that Define Functional Specificity", *EMBO J.*, 1986, 5(10), 2503–2512.

Ullrich, A. And Schlessinger, J., "Signal Transduction by Receptors with Tyrosine Kinase Activity", *Cell*, 1990, 61, 203–212.

Zhou–Li, F., et al., "Association of Insulin Receptor Substrate 1 with Simian Virus 40 Large T Antigen", *Mol. Cell Biol.*, 1995, 15, 4232–4239.

Cox et al., "Identification of a Peptide Recognized by Five Melanoma–Specific Human Cytotoxic T Cell Lines", *Science*, 1994, 264, 716–719.

D'Ambrosio et al., "A Soluble Insulin–like Growth Factor I Receptor That Induces Apoptosis for Tumor Cells in vivo and Inhibits Tumorigenesis", *Cancer Res.*, 1996, 56, 4013–4020.

Kawakami et al., "Identification of a human melanoma antigen recognized by tumor–infiltrating lymphocytes associated with in vivo tumor rejection", *Proc. Natl. Acad. Sci. USA*, 1994, 91, 6458–6462.

Mandelbolm et al., "CTL Induction by a tumour–associated antigen octapeptide derived from a murine lung carcinoma", *Nature*, 1994, 369, 67–71.

Resnicoff et al., "The Insulin–like Growth Factor I Receptor Protects Tumor Cells from Apoptosis in Vivo", *Cancer Res.*, 1995, 55, 2463–2469.

Resnicoff et al., "Correlation between Apoptosis, Tumorigenesis, and Levels of Insulin–like Growth Factor I Receptors", *Cancer Res.*, 1995, 55, 3739–3741.

James, W., "Towards gene–inhibition therapy: a review of progress and prospects in the field of antiviral antisense nucleic acids and ribozymes," *Antiviral Chem. & Chemotherapy*, 1991, 2(4), 191–214.

Lieberthal, W., et al., "Mechanisms of apoptosis and its potential role in renal tubular epithelial cell injury," *American J. Phys.*, 1996, 271(3 part 2), F477–F488.

Lavin, M.F., et al., "Role of protein kinase activity in apoptosis," *Experientia*, 1996, 52(10–11), 979–994.

Huybrechts, M., et al., "The diffusion chamber technique as an in vivo assay in mice for the effectiveness of antitumor agents," *Scand. J. Haem.*, 1979, 23(3), 223–226.

Hoeltzer, D., et al., "Low–dose ara–C in the treatment of acute leukemia cytotoxicity or differentiation induction," *Blut*, 1984, 48(4), 233–238.

Lahm, H. et al., "Growth Inhibition of Human Colorectal Carcinomas by a Monoclonal Antibody Directed Against the IGF–1 Receptor," *Eur. J. Cancer*, 1991, 27(Suppl. 3), Abstract No. 11.053.

Pietrzykowski, A. et al., "Inhibition of Growth of Prostatic Cancer Cell Lines by Peptide Analogues on Insulin–like Growth Factor 1," *Cancer Res.*, 1993, 53, 1102–1106.

Pietrzykowski, Z. et al., "Autocrine Growth of Cells Overexpressing the Human IGF–1 and IGF–1 Receptor Genes," *Federal of American Society for Experimental Biology*, 75th Annual Meeting, Atlanta, GA, 1991, Part 3, Abstract No. 7268.

Rohlik, Q. et al., "An Antibody to the Receptor for Insulin–like Growth Factor 1 Inhibits the Growth of MCF–7 Cells in Tissue Culture," *Biochem. Biophys. Res. Commun.*, 1987, 149(1), 276–281.

Shapiro, D. N. et al., "Antisense–mediated reduction in insulin–like growth factor–1 receptor expression suppresses the malignant phenotype of a human rhabdomyosarcoma," *Cancer Res.*, Eighty–Third Annual Meeting, 1992, 33, Abstract No. 2112.

Wickstrom, E. et al., "Antisense DNA Methylphosphonate Inhibition of C–MYC Gene Expression in Transgenic Mice," *FASEB J.*, 75th Annual Meeting, Atlanta, GA, 1991, Part 2, Abstract No. 6218.

Resnicoff, M. et al., "Regression of C6 rat brain tumors by cells expressing an antisense insulin–like growth factor I receptor RNA," *J. Exp. Therap. Oncol.*, 1996, 1, 385–389.

* cited by examiner

TTTTTTTTTTTTGAGAAAGGGAATTTCATCCCAAATAAAAGGAATGAAGTCTGGCTCCGGAGGAGGGTCCCG

```
             -30
             MetLysSerGlyGlySerGlyGlySerPro
             -20                                               -1  1   ← α subunit
             ThrSerLeuTrpGlyLeuPheLeuSerAlaAlaLeuSerLeuTrpProThrSerGlyGlyIleCysGlyGlyPro      150
             ACCTCGCTGTGGGGGCTCCCTGTTTCTCTCCGGCGCTCTGGCCGACGAGTGGAGAAATCTGCGGGCCA
                            10                              20                          30
             GlyIleAspIleArgAsnAspTyrGlnGlnLeuLysArgLeuLysLeuArgGluAsnCysThrValIleGluGlyTyrLeuHis
             GGCATCGACATCCGCAACGACTATCAGCAGCTGAAGCGCCTGAAGCTGAGAGAAAACTGCACGGTGATCGAGGGCTACCTCCAC
                                 40                            50
             IleLeuLeuIleSerLysAlaGluAspThrTyrArgSerTyrArgPheProLysLeuThrValIleThrGluTyrLys
             ATCCTGCTCATCTCCAAGGCCGAGGACACCTACCGCAGCTACAGGTTCCCCAAGCTCACGGTCATTACCGAGTACTTG
                   60                        70                          80
             LeuLeuPheArgValAlaGlyLeuGluSerLeuGlyLeuAspLeuPheProAsnLeuThrValIleThrValArgGlyTrpSerLysLeu
             CTGCTGTTCCGAGTGGCTGGCTGGAGAGCCTGGGACTGGACCTCTTCCCCAACCTCACGGTCATCCGGGGCTGGAAA
                       90                            100
             LeuPheTyrAsnTyrAlaLeuValIleLeuPheGluMetThrAsnLeuLysAspIleGlyIleGlyLeuTyrAsnLeuArgAsn
             CTCTTCTACAACTACGCCCTGGTCATCTTCGAGATGACCAACCTCAAGGATATTGGGCTTTACAACCTGAGGAAC
                               110                                    120                           130
             IleThrArgGlyAlaIleArgIleGluLeuSerThrValAspTrpSerLeuIle
             ATTACTCGGGGGGCCATCAGGATTGAGAAAAATGCTGACCTCTGTTACCTCTCCACTGTGGACTGGTCCCTGATC
             LeuAspAlaValSerAsnAsnTyrIleValGlyAsnLysProProLysGluLysGlyAspLeuCysGlyIleThr
                           140                        150                    160
             CTGGAAAAAACAATTCAGAAGGAAAACGCCCCAAGGAATAAAACCCCCAAAGGAATGGGGACCTGTCCAGGGACC
             MetGluLysThrThrIleAsnAsnGluTyrArgCysTrpThrThrAsnArg
                           170                            180
             ATGGAGGAAGCCGATGTGTGAGAAGAGACACCATCAACAATGAGTACTACAACTACCGCTGTTGGACCAAACCGC
```

FIG. 4A

```
                                                              200
                         190                                  CysCysHisProGluCys
CysGlnLysMetCysProSerThrCysGlyLysArgAlaCysThrGluAsnAsnGluCysCysHisProGluCys     750
TGCCAGAAAATGTGCCCAAGCACGTGCCTGGGAAGCGTGCACCGAGAACAATGAGTGCTGCCACCCCGAGTGC
                                                              230
          210                    220                          CysArgHisTyrTyrAlaGlyValCys
LeuGlySerCysSerAlaProAspAsnAspThrAlaCysValAlaCysArgHisTyrTyrAlaGlyValCys       900
CTGGGCAGCTGCAGCGCGCCTGACAACGACACGGCCTGTGTAGCTTGCCGCCACTACTACTATGCCGGTGTCTGT
                                                              250                    280
                                                              CysValAspArgAspPheCysAlaAsnIle
                                                                                     CysMetGlnGluCysProSerGly
VaIProAIaCysProProAsnThrTyrArgPheGluGlyTrpArgCysValAspArgAspPheCysAlaAsnIle     1050
GTGCCTGCCTGCCCGCCCAACACCTACAGGTTTGAGGGCTGGCGCTGTGTGGACCGTGACTTCTGCGCCAACATC
CysMetGlnGluCysProSerGly
LeuSerAlaGluSerSerAspSerGlyPheValIleHisAspGlyGluCysMetGlnGluCysProSerGly       
CTCAGCGCCGAGAGCAGCGACTCCGGGTTTGTGATCCACGACGGCGAGTGCATGCAGGAGTGCCCCTCGGGC
                                                              330
          290                    320                          CysGluGluGlu
PheIleArgAsnGlySerGlnSerMetTyrCysIleProCysGluGlyProCysProLysValCysGluGluGlu    1200
TTCATCCGCAACGGCAGCCAGAGCATGTACTGCATCCCTTGTGAAGGTCCTTGCCCGAAGGTCTGTGAGGAAGAA
          310                    340                          CysThrIlePheLysGlyAsnLeu
LysLysThrIleAspSerValThrSerAlaGlnMetLeuGlnGlyCysThrIlePheLysGlyAsnLeu
AAGAAAACAATTGATTCTGTTACTTCTGCTCAGATGCTCCAAGGATGCACCATCTTCAAGGGCAATTTG
                                                              380
          350                    370                          CysLeuIleLeuGluValValThr
LeuIleAsnIleArgArgGlyLysAsnAsnIleAlaSerGluLeuAsnPheMetGlyLeuIleLeuGluValValThr 1350
CTCATTAACATCCGACGGGGGAAGAATAACATTGCTTCAGAGCTTAACTTCATGGGGCTCATCGAGGTGGTGACG
          360                                                 380
GlyTyrValLysIleArgHisSerHisAlaLeuValSerLeuPheLeuSerLysAsnLeuAsnLeuArgLeuLeuGly
GGCTACGTGAAGATCCGCCATTCTCATGCCCTTGTCTCCTAAAAACTTCGCCTCATCCTAGGA
          390
GluGluGlnLeuGluGlyLysAsnTyrSerPheTyrValLeuAspAsnLeuGlnAsnLeuTrpAspAsp          
GAGGAGCAGCTAGAAGGGAAGAACTACTCCTTCTACGTCCTCGACAACCTGCAACTGTGGGACTGGGAC

FIG. 4B
```

```
     410                          420                         430
HisArgAsnLeuThrIleLysAlaGlyLysMetTyrPheAlaAsnProLysLeuCysValSerGluIleTyr
CACCGCAACCTGACCATCAAAGCAGGGAAAATGTACTTTGCTTTCAATCCCAAATTATGTGTTTCGAAATTTAC

ArgMetGluGluValThrGlyThrLysGlyArgGlnSerLysGlyAspIleAsnThrArgAsnAsnGlyGluArg       1500
     440                          450                         480
CGCATGGAGGAAGTGACGGGCACCAAAGGCCGCCAAAGCAAAGGGGACATAAACACCAGGAACAACGGGGAGAGA
                                  460      (2) 470
AlaSerCysGluSerAspValLeuHisPheThrSerLysAsnArgIleIleIleThrHisTrpHis
GCCTCCTGTGAAAGTGACGTCCTGCATTTCACCTCCAAGAATCGCATCATCATAACCCATGGCAC

ArgTyrArgProProAspTyrArgAspLeuIleSerPheThrValThrTyrLysGluAlaProPheLysAsnVal       1650
     490                          500                         530
CGGTACCGGCCCCCTGACTACAGGGATCTCATCAGTTTCACCGTTACTACAAGGAAGCACCCTTTAAGAATGTC
     510      (3)        520
ThrGluTyrAspGlyGlnAspAlaCysGlySerAsnSerTrpAsnMetValAspValAspLeuProProAsnLys
ACAGAGTATGATGGGCAGGATGCCTGTGGCTCCAACAGCTGGAACATGGTGGACGTGGACCTTCCGCCCAACAAG

AspValGluProGlyIleLeuLeuHisGlyLeuLysProTrpThrGlnTyrAlaValThrValLysGlnThr       1800
                                  550                         580
GACGTGGAGCCCGGCATCTTACTACATGGGCTGAAGCCCTGGACTCAGTACGCCGTTTACGTCAAGCAGACC
     560      570
LeuThrMetValGluAsnAspHisIleArgGlyAlaLysSerGlnLeuIleLeuTyrIleArgThrAsnAlaSerVal
CTCACCATGGTGGAGAACGACCATATCCGTGGGGCCAAGAGTCAGATCTTGTACATTCGCACCAATGCTTCAGTT

ProSerIleProLeuAspValLeuSerAlaSerAsnSerSerGlnLeuIleValLysTrpAsnProProSer       1950
                                                              630
CCTTCCATTCCTTTGGACGTCTTTCAGCATGGAACTCGAACTCCTCAGTTAATCGTGAAGTGGAACCCCCTCT
     610      (4) 590                   620
LeuProAsnGlyAsnLeuSerTyrTyrIleValArgTrpGlnArgGlnProGlnAspGlyTyrLeuTyrArgHis
CTGCCCAACGGGCAACCTGAGTTACTACATTGTGCGCTGGCAGCGCCAGGACGGCTACCTTTACCGGCAC
```

FIG. 4C

```
                    640                 650
AsnTyrCysSerLysAspLysIleProIleArgLysTyrAlaAspGlyThrIleAspIleGluValThrGlu
AATTACTGTCCAAAGACAAAATCCCATCAGGAAGTATGCCGACGGCACCATCGACATTGAGGAGGTCACAGAG   2100

660                 670                         680
AsnProLysThrGluValCysGlyGlyGluLysGlyProCysCysAlaCysProLysThrGluAlaGluLysGln
AACCCCAAGACTGAGGTGTGTGGGGAGAAGGGCCCTTGCTGCGCCTGCCCCAAAACTGAGGCCGAGAAGCAG   2250

700
AlaGluLysGlyGluAlaGluTyrArgLysValPheLysAsnPheLeuHisAsnSerIlePheValProArgPro
GCCGAGAAGGGAGAGGCTGAATACCGCAAAGTCTTTGAGAATTTCCTGCACAACTCCATCTTCGTGCCCAGACCT

710      β subunit          720                 730
GluArgLysGlyArgArgAspValMetGlnValAlaAlaAsnThrThrSerSerArgSerArgAsnThrThrAlaAla
GAAAGGAAGCGGAGAGATGTCATGCAAGTGGCCGCCAACACCACCAGCAGCAGGAGCAGGAACACCACGGCCGCA AspThrTyrAsnIleThrAspProGluLeuGluThrGluTyrProPhePheGluSerArgValAspAsnLys           2400
GACACCTACAACATCACCGACCCGGAGCTGGAGACAGAGTACCCCTTTTTTGAGAGCAGAGTGGATAACAAG 760                       770                 780
GluArgThrValIleSerAsnLeuArgProPheThrLeuTyrArgIleAspIleHisSerCysAsnHisGluAla
GAGAGAACTGTCATTTCTAACCTTCGGCCCTTCACATTGTACCGCATCGATATCCACAGCTGCAACCACGAGGCT GluLysLeuGlyCysSerAlaSerAsnPheValPheAlaArgThrMetProAlaGluGlyAlaAspIlePro            2550
GAGAAGCTGGGCTGCAGCGCCTCCAACTTCGTCTTTGCAAGGACTATGCCGCAGAAGGAGCAGATGACATTCCT 810                 820                         830
GlyProValThrAspLeuProArgProGluProAsnSerIlePheLeuLysTrpGluProGluProAsnGly
GGGCCAGTGACTGACCTGGGAGCCAAGGCCTGAAAACTCCATCTTTTTAAAGTGGCCGGAACCTGAGAATCCCAATGGA LeuIleLeuMetTyrGluIleLysTyrGlyLysSerArgGlnValSerArgGlyValSerArgGlnGluTyr              2700
TTGATTCTAATGTATGAAATAAAATACGGATCACAAGTTGAGGATCAGCGAGAATCAGGAATAC
```

FIG. 4D

```
                                                 880
     ArgLysTyrGlyGlyAlaAlaLysLeuAsnArgProGlyAsnTyrThrAlaArgIleGlnAlaThrSerLeu
     AGGAAGTATGGAGGGGCCAAGCTAAACCGGGAACTACACAGCCCGGATTCAGGCCACATCTC             2850
              860              870

SerGlyAsnGlySerTrpThrAspProValPhePheTyrValGlnAlaLysThrGlyTyrGluAsnPheIleHis
     TCTGGGAATGGGTCGTGGACAGATCCTGTTCTTCTATGTCCAGGCCAAAACAGGATATGAAAACTTCATCCAT
              890              900                                            930
                                                                               |
     LeuIleIleAlaLeuProValAlaValLeuLeuIleValGlyLeuValIleMetLeuTyrValPheHisArg
     CTGATCATCGCTCTGCCCGTCGCTGTCCTGTTGATCGTGGGAGGGTTGGTGATTATGCTGTACGTCTTCCATAGA
                      910              920
                                                                                3000
     LysArgAsnSerArgLeuGlyAsnGlyValLeuTyrAlaSerValAsnProGluTyrPheSerAlaAlaAsp
     AAGAGAAATAACAGCAGGCTGGGGAATGGAGTGCTGTATGCCTCTGTGAACCCGGAGTACTTCAGCGCTGCTGAT
              940                      950
                          *   *                                         980
     ValTyrValProAspGluTrpGluPheProArgGluLysLeuThrMetSerArgGluLeuGlyGlnGlySerPhe
     GTGTACGTTCCTGATGAGTGGGAGTTCCCTCGGGAGAAGCTCACCATGAGCCGGGAACTTGGGCAGGGGTCGTTT
              960                                  970

3150
                                                             1000
     GlyMetValTyrGluGlyGlyValAlaLysGlyValValLysAspGluProThrArgValAlaIleLysThrVal
     GGGATGGTCTATGAAGGAGGTGTGGCCAAGGGTGTGGTGAAAGATGAACCTACCAGAGTGGCCATTAAAACAGTG
                      990
                                                                      1030
     AsnGluAlaAlaSerMetArgGluArgIleGluPheLeuAsnGluAlaSerValMetLysGluPheAsnCysHis
     AACGAGGCCGCAAGCATGCGTGAGAGGATTGAGTTTCTCAACGAAGCTTCTGTGATGAAGGAGTTCAATTGTCAC
              1010                              1020
                                                                                3300
     HisValArgLeuLeuGlyValValSerGlnGlyGlnProThrLeuValIleMetGluLeuMetThrArgGly
     CATGTGCGGCTGCTGGGTGTGGTGTCCCAAGGCCAACACACTGGTCATCATGGAACTGATGACACGGGGC
              1040                      1050                            1080

AspLeuLysSerTyrLeuArgSerLeuArgProValLeuAlaProSerLeuSer
     GATCTCAAAAGTTATCTCCGGTCTCTGAGGCCAGTCCTAGCCACCTCCAAGCCTGAGC
              1060                      1070
```

FIG. 4E

```
                    1090
LysMetIleGlnMetAlaGlyGluIleAlaAspGlyMetAlaTyrLeuAsnAlaAsnLysPheValHisArgAsp
AAGATGATTCAGATGGCCGGAGAGATTGCAGACGGGATGGCATACCTCAACGCCAATAAGTTCGTCCACAGAGAC  3450
                                                  1130
LeuAlaAlaArgAsnCysMetValAlaGluAspPheThrValLysIleGlyAspPheGlyMetThrArgAspIle
CTTGCTGCCCGGAATTGCATGGTAGCCGAAGATTTCACAGTCAAAATCGGAGATTTTGGTATGACGCGAGATATC
                              1120
                    1140                                         1180
TyrGluThrAspTyrTyrArgLysGlyGlyLysGlyLeuLeuProValArgTrpMetSerProGluSerLeuLys
TATGAGACAGACTATTACCGGAAAGGGGGAAAGGGACTGCTGCCCGTGCGCTGGATGTCTCCTGAGTCCCTCAAG  3600
                    1140                              1170
AspGlyValPheThrThrTyrSerAspValTrpSerPheGlyValValLeuTrpGluIleAlaThrLeuAlaGlu
GATGGAGTCTTCACCACTTACTCGGACGTCTGGTCTTTCGGGGTCGTCCTCTGGGAGATCGCCACACTGGCCGAG
                              1170
                    1190                              1230
GlnProTyrGlnGlyLeuSerAsnGluGlnValLeuArgPheValMetGluGlyGlyLeuLeuAspLysProAsp
CAGCCCTACCAGGGCCTTGTCCAACGAGCAAGTCCTTCGTCATGGAGGGCGGGCCTTCTGGACAAGCCAGAC  3750
                                              1230
AsnCysProAspMetLeuPheGluLeuMetArgMetCysTrpGlnTyrAsnProLysMetArgProSerPheLeu
AACTGTCCTGACATGCTGTTTGAACTGATGCGCATGTGCTGGCAGTATAACCCCAAGATGAGGCCTTCCTTCCTG
                    1240                              1280
GluIleIleSerSerIleLysGluGluMetGluProGlyPheArgGluValSerPheTyrTyrSerGluGluAsn
GAGATCATCAGCAGCATCAAAGAGGAGATGGAGCCTGGCTTCCGGGAGGTCTCCTTCTACTACAGCGAGGAGAAC  3900
                    1260                              1280
LysLeuProGluGluLeuGluProGlyPheArgGluValAsnMetGluSerValProLeuAspProSerAlaSer
AAGCTGCCCGAGGAGCTGGAGCCCGGGAGCGTCCCCCTGGACCCCTCC
                              1270
                    1290                    1300
SerSerSerLeuProProAspArgHisSerGlyHisLysAlaGluAsnGlyProGlyProGlyValLeuVal
TCGTCCTCCCTGCCACTGCCGACACTCAGGACACAAGGCCGAGAACGGCCCCGGCCCTGGGGTGCTGGTC      4050
```

FIG. 4F

```
                    1310                                                1320                                             1330
LeuArgAlaSerPheAspGluArgGlnProTyrAlaHisMetAsnGlyGlyArgLysAsnGluArgAlaLeuPro
CTCCGGGCCAGCTTCGACGAGAGACAGCCTTACGCCCACATGAACGGGGGCCGCAAGAACGAGCGGGCCTTGCCG    4200

LeuProGlnSerSerThrCysEnd
CTGCCCCAGTCTTCTGACCTGCTGATCCTTGGATCCTGAATCTGTGCAAACAGTAACGTGTGCGCACGCGCAGCGG    4350

GGTGGGGGGGAGAGAGAGTTTTAACAATCCATTCACAAGCCTCCTGTACCTCAGTGGATCTTCAGTTCTGCCCT    4500

TGCTGCCCGCGGGAGACAGCTTCTCTGCAGTAAAACACATTTGGGATGTTCCTTTTTCAATATGCAAGCAGCTT    4650

TTTATTCCCTGCCCAAACCCTTAACTGACATGGGCCTTTAAGAACCTTAATGACAACACTTAATAGCAACAGAGC    4650

ACTTGAGAACCAGTCTCCTCACTCTGTCCCTGTCCCTTTCTCCTGTCTTCATAAC    4500

GGAAAAATAATTGCCACAGTCCAGCTCCAGCCCTTTTTATCAGTTTGAGGAAGTGGCTGTCCCTGTGGCCCC

ATCCAACCACTGTACACACCCGCCTGACACCGTGGGTCATTACAAAAAAACACGTTCATCCAAGGCTGTTACGC    4650

TTATCTTTCACCTTTCTAGGGACACATGAACTTTCTCCCTGATTCCTGTCCGTCGTGCGGAGGCATGGG

TGCCTAATTTTGCCAAAATCCTGAACTTTCTCCATTTGAGAGACACAGGTCTCATTGCTTCCATCCGACTGCCCCTGTGT    4800

TGAGCATGGCAGCTGGTTGCTCCATTTGAGAGACACAGGTCACACAGGCACACAGGCACACTCCGTCGGCGACACTGCCCCTGCTGT

GCTGCTCAAGGCCACAGGCACACAGGTCTTGCTTCTGACTAGATTATTATTGGGGAACTGGACACAATAG    4950

GTCTTTCTCTCAGTGAAGGTGGGGAGAAGCTGAACCGGC    4989
```

FIG. 4G

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 927 base pairs
      (B) TYPE: nucleic acid
      (C) STRANDEDNESS: single
      (D) TOPOLOGY: linear (xi) SEQUENCE DESCRIPTION: SEQ ID NO: 1:

```
CUUUGUUUUC UUUUCUUCCU CACAGACCUU CGGGCAAGGA CCUUCACAAG        50

GGAUGCAGUA CAUGCUCUGG CUGCCGUUGC GGAUGAAGCC CGAGGGGCAC       100

UCCUGCAUGC ACUCGCCGUC GUGGAUCACA AACCCCUCGG AGUCGCUGCU       150

CUCGGCGCUG AGGAUGUUGG CGCAGAAGUC ACGGUCCACA CAGCGCCAGC       200
```

-continued

```
CCUCAAACCU GUAGGUGUUG GGCGGGCAGG CAGGCACACA GACACCGGCA        250

UAGUAGUAGU GGCGGCAAGC UACACAGGCC GUGUCGUUGU CAGGCGCGCU        300

GCAGCUGCCC AGGCACUCGG GGUGGCAGCA CUCAUUGUUC UCGGUGCACG        350

CCCGCUUCCC ACACGUGCUU GGGCACAUUU UCUGGCAGCG GUUUGUGGUC        400

CAGCAGCGGU AGUUGUACUC AUUGUUGAUG GUGGUCUUCU CACACAUCGG        450

CUUCUCCUCC AUGGUCCCUG GACACAGGUC CCCACAUUCC UUUGGGGCU         500

UAUUCCCCAC AAUGUAGUUA UUGGACACCG CAUCCAGGAU CAGGGACCAG        550

UCCACAGUGG AGAGGUAACA GAGGUCAGCA UUUUUCACAA UCCUGAUGGC        600

CCCCCGAGUA AUGUUCCUCA GGUUGUAAAG CCCAAUAUCC UUGAGAUUGG        650

UCAUCUCGAA GAUGACCAGG GCGUAGUUGU AGAAGAGUUU CCAGCCGCGG        700

AUGACCGUGA GGUUGGGGAA GAGGUCUCCG AGGCUCUCGA GGCCAGCCAC        750

UCGGAACAGC AGCAAGUACU CGGUAAUGAC CGUGAGCUUG GGGAAGCGGU        800

AGCUGCGGUA GUCCUCGGCC UUGGAGAUGA GCAGGAUGUG GAGGUAGCCC        850

UCGAUCACCG UGCAGUUCUC CAGGCGCUUC AGCUGCUGAU AGUCGUUGCG        900

GAUGUCGAUG CCUGGCCCGC AGAUUUC                                 927
```

(2) INFORMATION FOR SEQ ID NO: 2:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 2:

```
TCCTCCGGAG CCAGACTT                                            18
```

(2) INFORMATION FOR SEQ ID NO: 3:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 3:

```
GGACCCTCCT CCGGAGCC                                            18
```

(2) INFORMATION FOR SEQ ID NO: 4:

(i) SEQUENCE CHARACTERISTICS:
        (A) LENGTH: 17
        (B) TYPE: nucleic acid
        (C) STRANDEDNESS: single
        (D) TOPOLOGY: linear (xi) SEQUENCE DESCRIPTION: SEQ ID NO: 4:

```
CCGGAGCCAG ACTTCAT                                             17
```

(2) INFORMATION FOR SEQ ID NO: 5:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 5:

CTGCTCCTCC TCTAGGATGA                                              20

(2) INFORMATION FOR SEQ ID NO: 6:

(i) SEQUENCE CHARACTERISTICS:
        (A) LENGTH: 15
        (B) TYPE: nucleic acid
        (C) STRANDEDNESS: single
        (D) TOPOLOGY: linear (xi) SEQUENCE DESCRIPTION: SEQ ID NO: 6:

CCCTCCTCCG GAGCC                                                   15

(2) INFORMATION FOR SEQ ID NO: 7:

(i) SEQUENCE CHARACTERISTICS:
        (A) LENGTH: 17
        (B) TYPE: nucleic acid
        (C) STRANDEDNESS: single
        (D) TOPOLOGY: linear (xi) SEQUENCE DESCRIPTION: SEQ ID NO: 7:

TACTTCAGAC CGAGGCC                                                 17

(2) INFORMATION FOR SEQ ID NO: 8:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 8:

CCGAGGCCTC CTCCCAGG                                                18

(2) INFORMATION FOR SEQ ID NO: 9:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO: 9:

TCCTCCGGAG CCAGACTT                                                18

(2) INFORMATION FOR SEQ ID NO: 10:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 10:

Tyr Leu Glu Pro Gly Pro Val Thr Ala
                5

(2) INFORMATION FOR SEQ ID NO: 11:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 11:

Leu Leu Asp Gly Thr Ala Thr Leu Arg Leu

```
                         5                    10
```

(2) INFORMATION FOR SEQ ID NO: 12:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 12:

```
Phe Glu Cys Asn Thr Ala Gln Pro Gly
                 5
```

(2) INFORMATION FOR SEQ ID NO: 13:

(i) SEQUENCE CHARACTERISTICS:
        (A) LENGTH: 9amino acids
        (B) TYPE: amino acid
        (D) TOPOLOGY: linear (xi) SEQUENCE DESCRIPTION: SEQ ID NO: 13:

```
Ala Thr Val Pro Gly Pro Glu Leu Tyr
                 5
```

(2) INFORMATION FOR SEQ ID NO: 14:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 14:

```
Leu Arg Leu Thr Ala Thr Gly Asp Leu Leu
                 5                    10
```

(2) INFORMATION FOR SEQ ID NO: 15:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 15:

```
Tyr Leu Glu Pro Gly Ala Val Thr Ala
                 5
```

(2) INFORMATION FOR SEQ ID NO: 16:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 16:

```
Tyr Leu Arg Pro Gly Pro Val Thr Ala
                 5
```

METHOD OF INDUCING RESISTANCE TO TUMOR GROWTH

CROSS REFERENCE TO RELATED APPLICATIONS

The present application is a continuation of U.S. Ser. No. 08/864,641 filed May 29, 1997, now issued Pat. No. 6,312,684, which is a continuation in part of U.S. Ser. No. 08/340,732 filed Nov. 16, 1994, now issued Pat. No. 5,714,170, and international application Ser. No. PCT/US95/14952 filed Nov. 15, 1995, each of which is incorporated herein by reference.

REFERENCE TO GOVERNMENT GRANTS

This invention was funded by National Institute of Health Grants GM 33694 and CA 56309. The U.S. government may have certain rights in the invention.

FIELD OF THE INVENTION

The present application is directed to inducing resistance to tumor growth by using diffusion chambers implanted in mammals.

BACKGROUND OF THE INVENTION

Traditional methods of treating tumors in mammals include procedures such as, for example, surgical removal of the tumor, injection or implantation of toxic treatments or syngeneic tissue samples, chemotherapy, and irradiation. The ultimate goal of each of these procedures is to reduce the growth of existing tumors, preferably abrogating tumor growth to the point of complete regression, and/or to induce resistance to future tumor growth. These procedures have numerous effects on tumor cells.

Tumors and other neoplastic tissues are known to undergo apoptosis spontaneously or in response to treatment. Examples include several types of leukemia, non-Hodgkin's lymphoma, prostate tumor, pancreatic cancer, basal and squamous cell carcinoma, mammary tumor, breast cancer, and fat pad sarcoma. Several anticancer drugs have been shown to induce apoptosis in target cells. Buttyan, et al., *Mol. Cell. Biol.*, 1989, 9, 3473–3481; Kaufmann, *Cancer Res.*, 1989, 49, 5870–5878; and Barry, et al., *Biochem. Pharmacol.*, 1990, 40, 2353–2362, all of which are incorporated herein by reference. Certain mildly adverse conditions can result in the injured cell dying by programmed cell death, including hyperthermia, hypothermia, ischemia, and exposure to irradiation, toxins, and chemicals. It should be noted that many of these treatments will also result in necrosis at higher doses, suggesting that mild injury to a cell might induce cell suicide, perhaps to prevent the inheritance of a mutation, while exposure to severe conditions leads directly to cell death by necrosis. However, the death process is difficult to observe due to the rapidity of the process and the reduced amount of inflammation. For these reasons, quantification of apoptosis is often difficult. A method of measuring the duration of the histologically visible stages of apoptosis (3 hours in normal rat liver) and a formula by which to calculate the cell loss rate by apoptosis is set forth by Bursch, et al., *Carcinogenesis*, 1990, 11, 847–853.

Evidence is also rapidly accumulating that growth factors and their receptors play a crucial role in the establishment and maintenance of transformed phenotypes. It is well established that growth factors play a crucial role in the establishment and maintenance of the transformed phenotype. Mouse embryo cells with a targeted disruption of the type 1 insulin-like growth factor receptor (IGF-IR) genes cannot be transformed by SV40 T antigen and/or an activated Ha-ras oncogene that easily transform embryo cells generated from their wild-type littermates. Sell, et al., *Proc. Natl. Acad. Sci. USA,* 1993, 90, 11217–11221; Sell, et al., *Mol. Cell. Biol.,* 1994, 14, 3604–3612; Valentinis, et al., *Oncogene,* 1994, 9, 825–831; and Coppola, et al., *Mol. Cell. Biol.,* 1994, 14, 4588–4595. Expression of an antisense RNA to the IGF-IR RNA in C6 rat glioblastoma cells not only abrogates tumorigenesis in syngeneic rats, but also causes complete regression of established wild type tumors. Resnicoff, et al., *Cancer Res.,* 1994a, 54, 2218–2222 and Resnicoff, et al., *Cancer Res.,* 1994b, 54, 4848–4850. Related to this finding is also the report by Harrington, et al. (*EMBO J.,* 1994, 13, 3286–3295), that IGF-I (and PDGF) protect cells from c-myc induced apoptosis. A decrease in cell death rate in tumors could certainly be an important mechanism for tumor growth. Baserga, *The Biology of Cell Reproduction*, Harvard University Press, Cambridge, Mass., 1985. Cells expressing an antisense RNA to the IGF-IR RNA or cells pre-incubated with antisense oligodeoxynucleotides to the IGF-IR RNA completely lose their tumorigenicity when injected in either syngeneic or nude mice. Resnicoff et al., 1994a, 1994b. The injected cells were suspected of undergoing apoptosis or, at any rate, some form of cell death. Dying cells, however, are very difficult to demonstrate, because dying cells, especially in vivo, disappear very rapidly, and one is left with nothing to examine.

The importance of the IGF-I receptor in the control of cell proliferation is also supported by considerable evidence: 1) many cell types in culture are stimulated to grow by IGF-I (Goldring, et al., *Crit. Rev. Eukaryot. Gene Expr.,* 1991, 1, 301–326 and Baserga, et al., *Crit. Rev. Eukaryot. Gene Expr.,* 1993, 3, 47–61), and these cell types include human diploid fibroblasts, epithelial cells, smooth muscle cells, T lymphocytes, myeloid cells, chondrocytes, osteoblasts as well as the stem cells of the bone marrow; 2) interference with the function of the IGF-I receptor leads to inhibition of cell growth. This has been demonstrated by using antisense expression vectors or antisense oligodeoxynucleotides to the IGF-I receptor RNA: the antisense strategy was successful in inhibiting cellular proliferation in several normal cell types and in human tumor cell lines (Baserga, et al., 1994, supra.); and 3) growth can also be inhibited using peptide analogues of IGF-I (Pietrzkowski, et al., *Cell Growth & Diff.,* 1992a, 3, 199–205 and Pietrzkowski, et al., *Mol. Cell. Biol.,* 1992b, 12, 3883–3889), or a vector expressing an antisense RNA to the IGF-I RNA (Trojan, et al., 1993, supra.). The IGF autocrine or paracrine loop is also involved in the growth promoting effect of other growth factors, hormones (for instance, growth hormone and estrogens), and oncogenes like SV40 T antigen and c-myb, and in tumor suppression, as in the case of WT1. Baserga, et al., 1994, supra.

Testing agents such as, for example, growth factors and growth factor receptors for their ability to maintain or suppress transformed phenotypes remains difficult. In order to obtain an accurate account of the tumor suppressive ability, testing should be performed in vivo. Therapies such as direct injection or implantation of toxic treatments, tissue samples, and chemotherapy often jeopardizes the overall health of the patient. However, the present invention provides a method of inducing resistance to tumor growth with markedly reduced side effects to the patient.

SUMMARY OF THE INVENTION

The present invention is directed to a method of inducing resistance to tumor growth in a mammal comprising pretreating tumor cells in vitro with a pro-apoptotic agent, placing the pretreated tumor cells in a diffusion chamber thereby producing a tumor cell-containing diffusion chamber, and inserting the tumor cell-containing diffusion chamber into the mammal for a therapeutically effective time thereby inducing resistance to tumor growth.

The present invention is also related to a method of screening test compounds for anti-cancer activity in a mammal comprising providing an in vitro tumor cell culture supplemented with a test compound, placing the tumor cells into a diffusion chamber thereby producing a tumor cell-containing diffusion chamber, inserting the tumor cell-containing diffusion chamber into the mammal for a period of time, and removing the tumor cell-containing diffusion chamber and evaluating the anti-cancer effects of the test compound.

BRIEF DESCRIPTION OF THE FIGURES

FIGS. 4A–4G provide the amino acid and nucleotide sequence of IGF-1 receptor.

DETAILED DESCRIPTION OF THE INVENTION

Figure 1:
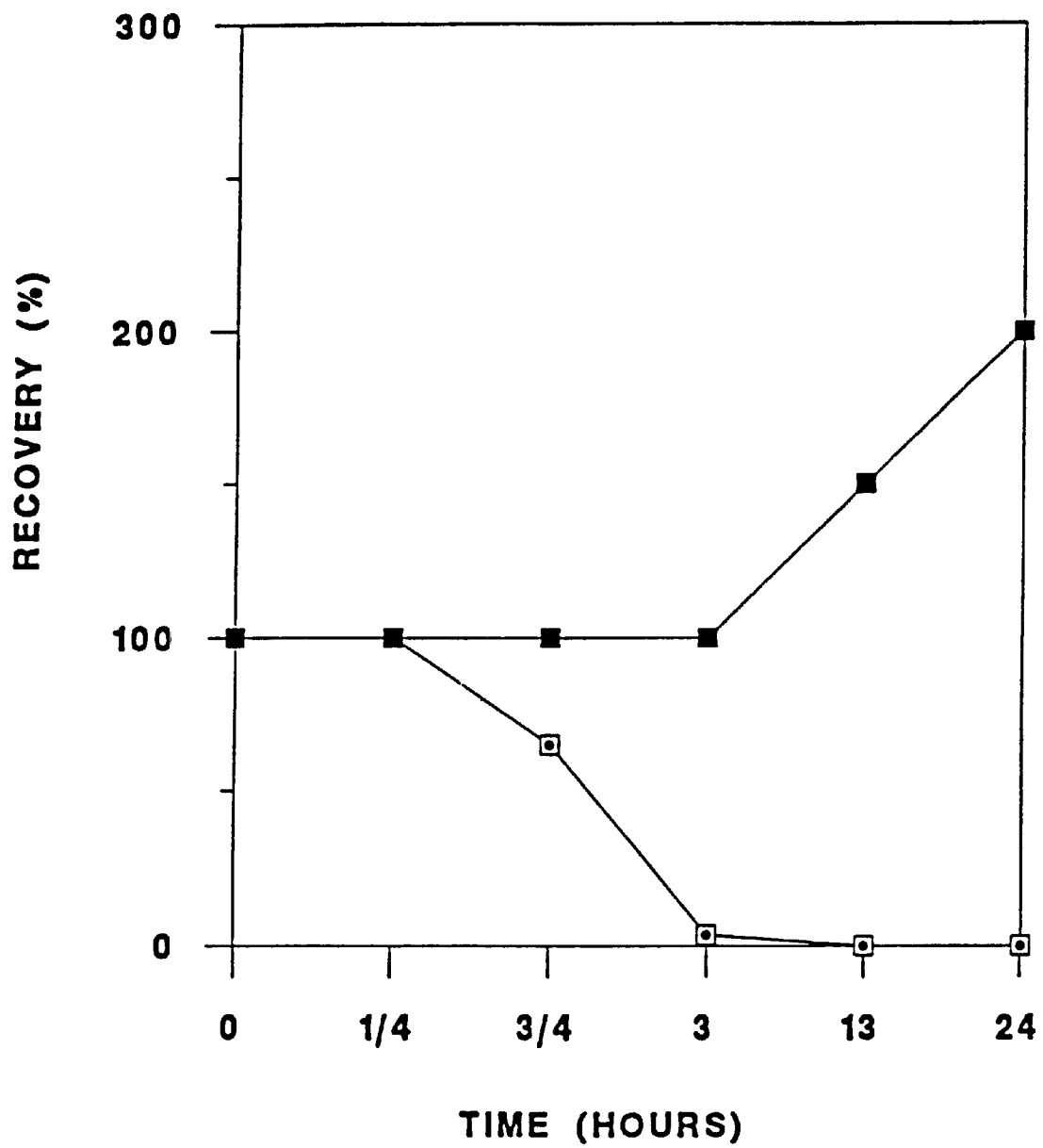
FIG. 1 is a graph representing the survival of C6 rat glioblastoma cells in diffusion chambers. Three cell lines were used: wild type C6 cells, and C6 cells stably transfected with either a sense or an antisense RNA to the IGF-I receptor RNA (Resnicoff, et al. 1994a and 1994b, both of which are incorporated herein by reference). $5 \times 10^5$ cells were inoculated in each chamber and the number of cells recovered was determined at the intervals indicated on the abscissa. Closed squares: wild type or sense cells (the curves were superimposable); open squares: antisense cells. The recovery is expressed as percentage of cells inoculated.

The present invention is directed to a method of inducing resistance to tumor growth in a mammal comprising pretreating tumor cells in vitro with a pro-apoptotic agent, placing the pretreated tumor cells in a diffusion chamber thereby producing a tumor cell-containing diffusion chamber, and inserting the tumor cell-containing diffusion chamber into the mammal for a therapeutically effective time thereby inducing resistance to tumor growth. Mammals subsequently challenged with wild-type tumor cells are resistant to the tumor cells. In addition, regression of already established tumors is evidenced.

The phrase "tumor cells," "tumors," and "cancer cells" are used interchangeably throughout the present application and include, but are not limited to, autografts, allografts, syngeneic, non-syngeneic and xenografts. Tumor cells used in the methods of the present invention can be cultured in vitro in a medium supplemented with a pro-apoptotic agent and subsequently transferred to a diffusion chamber. Tumor cells include any type of cell which upon apoptosis induces resistance to tumor growth, including and not limited to tumor cells. Preferably, treated tumor cells are placed in a diffusion chamber which is implanted in a mammal, wherein the tumor cells may preferably be the same type of tumor to which resistance is induced. However, an embodiment of the present invention includes tumors cultured in a diffusion chamber which are of a different type than the tumor to which resistance is granted. In addition, any type of tumor or cancer cell which undergoes apoptosis and induces resistance to tumor growth is useful in the present invention. Tumors which are treatable with the methods of the present invention may be primary or secondary, benign, malignant, metastatic, or micrometastatic tumors. Tumors treatable with the methods of the present invention include, but are not limited to, melanoma, prostate, ovary, mammary, pancreatic, lungs, colon, and smooth muscle tumors, as well as cells from glioblastoma, bone marrow stem cells, hematopoietic cells, osteoblasts, epithelial cells, fibroblasts, as well as any other tumor cells which undergo apoptosis and induce resistance to tumor cells.

For purposes of the present invention, mammals include and are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

The pro-apoptotic agents used in the methods of the present invention induce cell death, or apoptosis, of the tumor cells in the diffusion chamber in vivo. Apoptosis, for purposes of the present invention, is defined as cell death and includes, but is not limited to, regression of primary and metastatic tumors. Apoptosis is a programmed cell death which is a widespread phenomenon that plays a crucial role in the myriad of physiological and pathological processes. There exists a homeostatic control of cell number thought to result from the dynamic balance between cell proliferation and cell death. Necrosis is an accidental cell death which is the cell's response to a variety of harmful conditions and toxic substances. Apoptosis, morphologically distinct from necrosis, is a spontaneous form of cell death that occurs in many different tissues under various conditions. This type of cell death typically occurs in scattered cells and progresses so rapidly it is difficult to observe.

The cell death process of apoptosis occurs in two stages. The cell undergoes nuclear and cytoplasmic condensation, eventually breaking into a number of membrane-bound fragments containing structurally intact apoptotic bodies, which are phagocytosed by neighboring cells and rapidly degraded. Apoptosis is observed in many different tissues, healthy and neoplastic, adult and embryonic. Death occurs spontaneously, or is induced by physiological or noxious agents. Apoptosis is a basic physiological process that plays a major role in the regulation of cell populations.

Pro-apoptotic agents which supplement the culture medium of the tumor cells in vitro are preferably agents which induce cell death in vivo. A pro-apoptotic agent, for purposes of the present invention, is an agent which causes death of the tumor cells in the diffusion chamber in vivo such that the cell death has a tumor growth inhibiting effect, i.e., a resistant effect, on a tumor or tumors in the mammal in which the diffusion chamber is inserted. Such pro-apoptotic agents include, but are not limited to, nucleic acid molecules, proteins or peptides, non-protein or non-polynucleotide compounds, and physical conditions.

Pro-apoptotic agents, or apoptosis-inducing agents, which induce apoptosis of tumor cells in vivo include, for example, nucleic acid molecules. In one embodiment of the invention, the nucleic acid molecule is an oligonucleotide directed against DNA or RNA of a growth factor or growth factor receptor, such as, for example, insulin growth factor-1 receptor (IGF-IR). Most preferably, the oligonucleotide is directed against DNA or RNA of IGF-IR. The oligonucleotide can be directed to any portion of IGF-IR DNA or RNA. Preferably, the nucleotide sequence of the oligonucleotide includes, but is not limited to, nucleotide sequences complementary to codons 1-309 shown in FIGS. 4A–4G (SEQ ID NO: 1), comprising either RNA or DNA. The antisense oligonucleotides may also comprise nucleotide sequences complementary to portions of codons 1-309. In addition, mismatches within the nucleotide sequence of the oligonucleotide complementary to codons 1 to 309 are also within the scope of the invention. An oligonucleotide complementary to nucleotides −29 to −24 of the IGF-IR signal sequence (SEQ ID NO: 2) comprising DNA or RNA is also within the scope of the present invention. The signal sequence of IGF-IR is a 30 amino acid sequence. Contemplated by this definition are fragments of oligonucleotides within the 30 amino acid signal sequence. Alternatively, fragments of oligos within SEQ ID NO: 2 are also contemplated. Additional oligonucleotides of the invention include, but are not limited to, oligonucleotides comprising the following nucleotide sequences: GGACCCTCCTCCGGAGCC (SEQ ID NO: 3), CCGGAGCCAGACTTCAT (SEQ ID NO: 4), CTGCTCCTCCTCTAGGATGA (SEQ ID NO: 5)7 CCCTCCTCCGGAGCC (SEQ ID NO: 6), TACTTCAGACCGAGGCC (SEQ ID NO: 7), CCGAGGCCTCCTCCAGG (SEQ ID NO: 8), and TCCTCCGGAGCCAGACTT (SEQ ID NO: 9).

In another preferred embodiment of the invention, the nucleic acid molecule is a vector which produces an oligonucleotide directed against DNA or RNA of a growth factor or growth factor receptor such as, for example, SEQ ID Numbers 1–9. The nucleic acid molecule complementary to a portion of IGF-IR RNA or DNA is inserted into an appropriate delivery vehicle, such as, for example, an expression plasmid, cosmid, YAC vector, and the like. Almost any delivery vehicle can be used for introducing nucleic acids into tumor cells. Recombinant nucleic acid molecules (or recombinant vectors) include, for example, plasmid DNA vectors, cDNA-containing liposomes, artificial viruses, nanoparticles, and the like. It is also contemplated that vectors expressing the oligonucleotides can be injected directly into the tumor cells.

The regulatory elements of the recombinant nucleic acid molecules of the invention are capable of directing expression in mammalian tumor cells, preferably human tumor cells. The regulatory elements include a promoter and a polyadenylation signal. In addition, other elements, such as a Kozak region, may also be included in the recombinant nucleic acid molecule. Examples of polyadenylation signals useful to practice the present invention include, but are not limited to, SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, can be used.

The promoters useful in constructing the recombinant nucleic acid molecules of the invention may be constitutive or inducible. A constitutive promoter is expressed under all conditions of cell growth. Exemplary constitutive promoters include the promoters for the following genes: hypoxanthine phosphoribosyl transferase (HPRT), adenosine deaminase, pyruvate kinase, β-actin, human myosin, human hemoglobin, human muscle creatine, and others. In addition, many viral promoters function constitutively in eukaryotic cells, and include, but are not limited to, the early and late promoters of SV40, the Mouse Mammary Tumor Virus (MMTV) promoter, the long terminal repeats (LTRs) of Maloney leukemia virus, Human Immunodeficiency Virus (HIV), Cytomegalovirus (CMV) immediate early promoter, Epstein Barr Virus (EBV), Rous Sarcoma Virus (RSV), and other retroviruses, and the thymidine kinase promoter of herpes simplex virus. Other promoters are known to those of ordinary skill in the art.

Inducible promoters are expressed in the presence of an inducing agent. For example, the metallothionein promoter is induced to promote (increase) transcription in the presence of certain metal ions, and the Drosophila HSP70 promoter. Other inducible promoters are known to those of ordinary skill in the art.

Recombinant nucleic acid molecules comprising oligonucleotides of the invention can be introduced into a tumor cell or "contacted" by a tumor cell by, for example, transfection or transduction procedures. Transfection refers to the acquisition by a cell of new genetic material by incorporation of added nucleic acid molecules. Transfection can occur by physical or chemical methods. Many transfection techniques are known to those of ordinary skill in the art including: calcium phosphate DNA co-precipitation; DEAE-dextran DNA transfection; electroporation; naked plasmid adsorption, and cationic liposome-mediated transfection. Transduction refers to the process of transferring nucleic acid into a cell using a DNA or RNA virus. Suitable viral vectors for use as transducing agents include, but are not limited to, retroviral vectors, adeno associated viral vectors, vaccinia viruses, and Semliki Forest virus vectors.

In a preferred embodiment of the invention, recombinant vectors comprising oligonucleotides directed to DNA or RNA of IGF-IR, which are described, for example, in Resnicoff, et al. (1994a, 1994b, supra), both of which are incorporated herein by reference, are used. Briefly, plasmid HSP/IGF-IR AS expresses an antisense transcript 309 bp in length directed to IGF-IR RNA, under the control of a Drosophila HSP70 promoter. The hepatitis B polyadenylation signal sequence and a neomycin-resistance gene under the control of the SV40 promoter are present at the 3' termini of the 309 bp IGF-IR fragment. One skilled in the art can readily prepare additional vectors producing any of the oligonucleotides of the invention.

In other embodiments of the invention, the pro-apoptotic agents comprise proteins or peptides such as, for example, associated dominant negative mutants of IGF-IR and MHC class I peptides. Dominant negative mutants of IGF-IR include, for example, soluble IGF-IR, described in D'Ambrosio, et al., *Cancer Res.,* 1996, 56, 4013–4020, incorporated herein by reference, and myristylated C-terminus of IGF-IR (MyCF). MHC class I associated peptides include, for example, Tyr-Leu-Glu-Pro-Gly-Pro-Val-Thr-Ala (SEQ ID NO: 10) recognized by melanoma-specific CTL lines (Cox, et al., *Science,* 1994, 264, 716–719), Leu-Leu-Asp-Gly-Thr-Ala-Thr-Leu-Arg-Leu (SEQ ID NO: 11) derived from gp100 and involved in regression of human melanoma (Kawakami, et al., *Proc. Natl. Acad. Sci. USA,* 1994, 91, 6458–6462), and Phe-Glu-Cys-Asn-Thr-Ala-Gln-Pro-Gly (SEQ ID NO: 12) derived from connexin 37 and induces CTL responses against murine lung carcinoma (Mandelbolm, et al., *Nature,* 1994, 369, 67–71). In addition, inverted D-amino acid anologs of the above-identified peptides, such as Ala-Thr-Val-Pro-Gly-Pro-Glu-Leu-Tyr (SEQ ID NO: 13) and Leu-Arg-Leu-Thr-Ala-Thr-Gly-Asp-Leu-Leu (SEQ ID NO: 14), are also active. Amino acid substitutions are also contemplated by the present invention. The peptides of the present invention can be made synthetically as is well known to those skilled in the art.

In other embodiments of the invention, the pro-apoptotic agents comprise non-protein or non-polynucleotide compounds such as, for example, chemotherapeutic compounds or synthetic chemical compounds. Preferably, chemotherapeutic compounds include, for example, etoposide, cisplatin, camptothecin, and tumor necrosis factor alpha (TNF-α).

In other embodiments of the invention, the pro-apoptotic agents comprise physical conditions such as, for example, hyperthermia, hypothermia, ischemia, and ionizing irradiation. In embodiments where the tumor cells are exposed to such conditions, the condition is defined for purposes of the present invention as an agent, an apoptosis-inducing agent.

Therapeutically effective doses of the pro-apoptotic agents or apoptotic-inducing agents will be about that of the drugs alone; dosages will be set with regard to weight, and clinical condition of the patient. The proportional ratio of active ingredient to culture medium will naturally depend on the chemical nature, solubility, and stability of the compounds, as well as the dosage contemplated. The culture medium is also pharmaceutically acceptable. The apoptosis-inducing agents of the invention can be used alone or in combination with other apoptosis-inducing agents.

The present invention authenticates the importance of agents, such as IGF-IR, in the growth of tumor cells, and establishes: 1) a decrease in the number of IGF-IRs, brought about by antisense strategies, causes massive cell death in vivo. This is true of several cell lines, including a human melanoma cell line; 2) the mechanism of cell death is apoptosis; 3) a decrease in the number of receptors has an inhibitory effect on growth in vitro, but is much more effective in vivo, because of the massive cell death. IGF-IR protects tumor cells against cell death in vivo.

Tumorous tissue may be excised from the mammal or patient in which the diffusion chamber will be inserted or from another source which has been cultured in vitro. The tumor cells are cultured in vitro and are supplemented with a pro-apoptotic agent such as, for example, an antisense sequence for a cell growth factor or cell growth factor receptor, for a period of time, preferably 3 to 48 hours, more preferably 24 hours. Prior to culture in vitro, the tumor cells may be gently dissociated with trypsin. The tumor cells are washed and placed in a diffusion chamber which is then implanted into a mammal or patient for a therapeutically effective amount of time such that apoptosis of the tumor cells is induced in vivo, thereby inducing resistance to tumor growth.

One important advantage of the present invention is that toxic treatments to the tumor cells such as, for example, treatment with irradiation or chemotherapeutic compounds, are performed in vitro thereby eliminating toxicity to the host mammal. In addition, tumor cells may be placed into culture in a diffusion chamber and the chamber directly implanted into a mammal, thus eliminating the possibility of physical spreading of the tumor cells which may be associated with direct injection of tumor cells into a mammal.

The present invention employs the use of a diffusion chamber, in which the cells are contained. Cells are impermeable to a filter fitted on the diffusion chamber; they cannot leave or enter the chamber. The filter on the diffusion chamber has pores in the size range of about 0.25 µm or smaller, preferably about 0.1 µm in diameter. Lange, et al., *J. Immunol.*, 1994, 153, 205–211 and Lanza, et al., *Transplantation*, 1994, 57, 1371–1375, both of which are incorporated herein by reference in their entirety. Accordingly, cell death or apoptosis, can be quantitatively determined. The use of a diffusion chamber can be extended to other cell lines, even non-syngeneic, and even from different species, because of the rapidity with which cell death occurs, about 24 hours, well before any immune reaction could be established. Indeed, 3 types of cells with an intact number of IGF-IRs (human melanoma, rat rhabdomyosarcoma and murine p6 cells), double in number in 24 hours, regardless of whether they are syngeneic or not, while cells with decreased number of IGF-IRS, die. The diffusion chambers may be useful to study other types of cell death, induced by a variety of agents, as shown in the present invention by the massive apoptosis induced by etoposide on wild type C6 cells in vivo.

Diffusion chambers useful in the present invention include any chamber which does not allow passage of cells between the chamber and the mammal in which it is implanted, however, permits interchange and passage of factors between the chamber and the mammal. The chamber may allow for multiple and sequential sampling of the contents, without contamination and without sacrificing the mammal, therefore significantly reducing the number of implantation procedures performed on the mammal.

Figure 3:
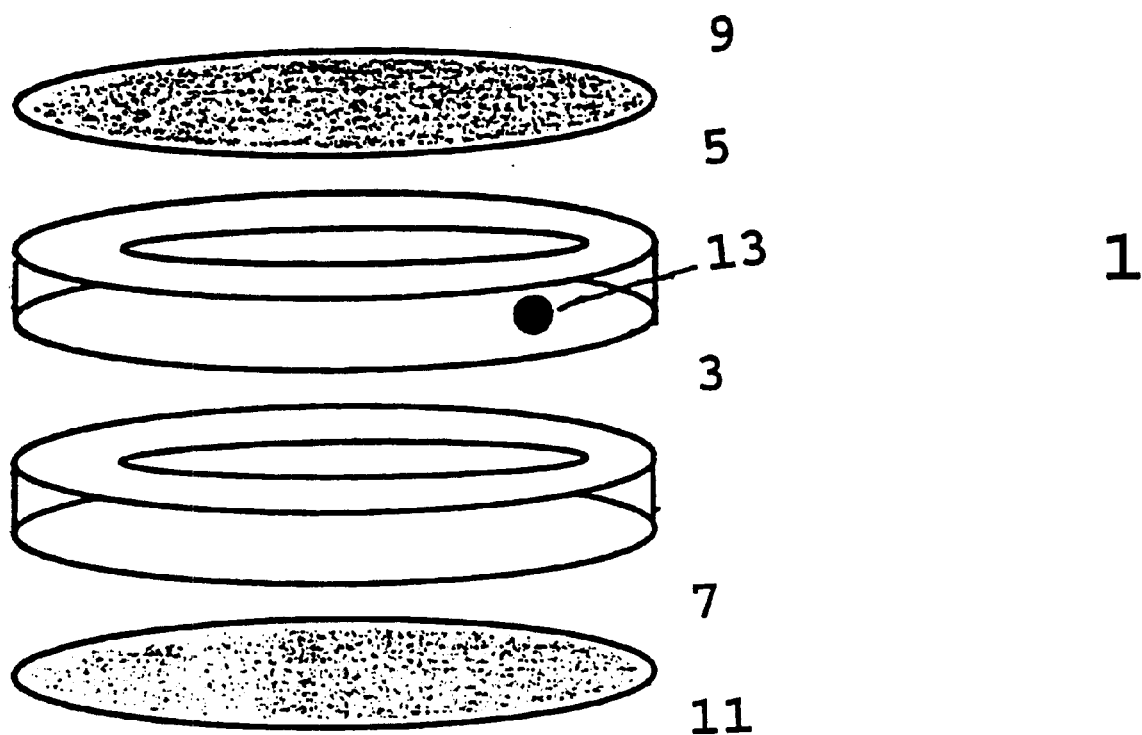
FIG. 3 shows a schematic illustration of a diffusion chamber.

Referring to FIG. 3, the diffusion chamber (1) may have a chamber barrel (3) having two ends, a first end (5) and a second end (7). The barrel may be comprised of one or more rings secured together by non-toxic means. The chamber is fitted at each end with a filter, a first filter (9) and a second filter (11). The filters are porous to factors such that the factors may pass between the chamber and the mammal. The filter pores size may be about 0.25 µm or smaller, preferably about 0.1 µm. The filters may be made of plastic, teflon, polyester, or any inert material which is strong, flexible and able to withstand chemical treatments. The filters may be secured in position with rubber gaskets which may also provide a tighter seal. On the barrel portion of the chamber, an opening (13) is provided which may be covered by a cap which is accessed from outside of the mammal's body once the chamber is implanted, thus allowing the diffusion chamber to be refilled. The cap may be screw on type of self sealing rubber and fitted to the opening. Sampling of the chamber contents may thus be performed by accessing the opening by removing the cap on the outside of the mammal's body and inserting an ordinary needle and syringe. The chamber may be made of any substance, such as and not limited to plastic, teflon, lucite, titanium, or any inert material, which is non-toxic to, and well tolerated by, mammals. In addition, the chambers should be able to survive sterilization.

The chamber may be implanted in the following non-limiting ways: subcutaneously or intraperitoneally, for example. The chamber may be removed about 24 to about 30 hours after implantation. Alternatively, a refillable chamber may be employed such that the chamber may be re-used for treatments and emptied following treatments.

Another embodiment of the present invention provides an in vivo method of screening agents for tumor resistance-inducing activity or anti-cancer therapeutic activity such as, for example, apoptosis activity. Tumor cells in media are cultured in the presence of a test compound. Contacting of cells with the test compound may be by direct delivery to the tumor cells in vitro or the test compound may be delivered to the test animal as a pharmaceutical formulation. After culture for about 24 hours in vitro, the tumor cells are washed with phosphate buffered saline and transferred to the diffusion chamber, which is subsequently implanted into a test animal, such as a rat or mouse, or other suitable mammal. The test compound is evaluated for anti-cancer efficacy or tumor resistance-inducing activity, i.e., apoptosis activity as described herein. The uniqueness of testing potential therapeutic agents in this manner provides the following advantages: 1) because the diffusion chamber confines the cells, they can be examined for changes, either morphological or biochemical or molecular; 2) testing in this manner is quick, i.e., 24 to 48 hours, thus it can be also done with non-syngeneic tumor cells, since the testing is over before any immune reaction may occur; and 3) cells are much more sensitive to apoptotic agents in vivo than in vitro; contacting tumor cells in vitro often leads to the engagement of the apoptosis inducible machinery without a fully working apoptotic mechanism, thus resulting in lack of apoptosis; thus, these agents should be tested in vivo. Conditions that in vitro, in monolayer cultures, only result in inhibition of IGF-I-mediated growth, an inhibition often very modest, will cause massive (about 100-fold) apoptosis in vivo. Resnicoff, et al., *Cancer Res.*, 1995, 55, 2463; and Resnicoff, et al., *Cancer Res.*, 1995, 55, 3739.

Apoptosis can be determined by methods such as, for example, DNA ladder, electron or light microscopy, flow cytometry, and different commercially available kits for the determination of apoptosis. Thus, use of diffusion chambers to test agents for anti-cancer efficacy would save time and money and provide more accurate results that testing of the same agents in vitro. Tumor resistance-inducing activity can be examined by subsequent challenge of the mammal with tumor cells and evaluating the resistance of the mammal to the tumor cells as determined by inhibition of growth of the tumor cells.

The following examples are illustrative but are not meant to be limiting of the invention.

EXAMPLES

Example 1

General Procedures
Tumor Cell Lines

The C6 rat glioblastoma cell line was used in this experiment. The C6 cell line is syngeneic in BD-IX rats (Charles River Breeders Laboratories, Boston, Mass.). This cell line has been described in detail by Trojan, et al., *Science*, 1993, 259, 94–97; Resnicoff, et al., *Cancer Res.*, 1994a, 54, 2218–2222; Resnicoff, et al., *Cancer Res.*, 1994b, 54, 4848–4850; Trojan, et al., 1992, supra, the disclosures of which are hereby incorporated by reference in their entirety. Two cell lines derived from C6 cells were also used, one expressing an antisense RNA to the IGF-IR RNA, and a control one expressing a sense RNA. Both cell lines were characterized by Resnicoff, et al. (1994a, 1994b, supra), incorporated herein by reference in their entirety. Other cell lines used were a human melanoma cell line, FO-1, and a rat rhabdomyosarcoma cell line, BA1112 (Martin, et al., *Eur. J. Cancer Clin. Oncol.*, 1983, 19, 791–797, incorporated herein by reference in its entirety). For OF-1 and BA 1112 cell lines, wild type cells were used, cells expressing sense and cells expressing antisense RNA to the IGF-IR RNA. The plasmids used and their effect on the number of IGF-I receptors have been described by Resnicoff, et al., *Cancer Res.*, 1994a, 5, 2218–2222, incorporated herein by reference in its entirety. The cells were pre-incubated at 39° C. for 24 hours, before inoculation in the diffusion chambers.

Cells were passaged in RPMI 1640 supplemented with 5% calf serum and 5% fetal bovine serum. $8 \times 10^4$ cells were plated in 35 mm dishes in 10% serum; after 12 hours, the growth medium was removed and replaced with serum-free medium supplemented with 0.1% bovine serum albumin (fraction V) and 1.0 $\mu$M ferrous sulfate, with or without IGF-1 (10 ng/ml), as disclosed by Resnicoff, et al., *Cancer Res.*, 1994a, 5, 2218–2222, incorporated herein by reference in its entirety.

Balb/c 3T3 are 3T3 cells, passaged for several years, and p6 cells are Balb/c 3T3 cells stably transfected with, and overexpressing a human IGF-IR cDNA. Pietrzkowski, et al., *Cell Growth Diff.*, 1992a, 3, 199–205, incorporated herein by reference in its entirety. (tsA)R– and (tsA)R+ cells have been described by Sell, et al., *Proc. Natl. Acad. Sci. USA*, 1993, 90, 11217–11221. (tsa)R– cells have no IGF-I receptors, while (tsa)R+ 1 cells overexpress human IGF-IR cDNA. Both (tsa)R– and (tsa)R+ cells express SV40 T antigen.

The number of IGF-I receptors in cells expressing an antisense RNA to the IGF-IR RNA, or in wild type cells treated with antisense oligodeoxynucleotides, is decreased by about 60–70%. Pietrzkowski, et al., *Cell Growth Diff.*, 1992, 3, 199–205 and Resnicoff, et al., 1994a, 1994b, incorporated herein by reference in their entirety.
Oligodeoxynucleotides The antisense oligodeoxynucleotide used is set forth in SEQ ID NO: 2, a DNA oligonucleotide to nucleotides –29 to –24 of the IGF-1R signal sequence. The control oligodeoxynucleotide was a mixture of random mismatchings at each nucleic acid position of the –29 to –24 signal sequence. Both oligonucleotides were phosphorothioates and were provided by Lynx Therapeutics (Hayward, Calif.).

The wild type C6 rat glioblastoma cells were incubated with antisense oligodeoxynucleotides to the IGF-IR RNA are shown in Table 1. The antisense oligonucleotide exerts a 50% inhibition in the growth of C6 cells, while the control oligonucleotide is totally inactive.

TABLE 1

Effect of an Antisense Oligodeoxynucleotide
on the Growth of C6 Glioblastoma Cells in vitro

| conditions | number of cells × $10^4$ |
|---|---|
| serum-free medium | 21.0 ± 0.6 |
| serum-free medium + sense | 21.8 ± 0.5 |
| serum-free medium + antisense | 15.4 ± 0.9 |
| serum-free medium + IGF-I | 29.9 ± 0.7 |
| same + sense oligo | 28.4 ± 0.3 |
| same + antisense oligo | 13.4 ± 0.6 |

The number of cells was determined 48 hours after plating, and each number is the average (with standard deviation) of triplicates. The concentration of IGF-I was 10 ng/ml. The concentration of oligodeoxynucleotides was 120 $\mu$g/ml.
Diffusion Chamber Diffusion chambers were constructed from 14 mm Lucite rings with 0.1 $\mu$m pore-sized hydrophilic Durapore membranes (Millipore, Bedford, Mass.). The diffusion chambers were sterilized with ethylene oxide prior to use. After the cells were pre-incubated for 24 hours according to the methods of Resnicoff, et al., 1994a, incorporated herein by reference in its entirety, and as set forth above, they were placed into the chambers, which were then inserted into the subcutaneous tissue of rats, under anesthesia with Halothane (inhalant). This procedure was repeated for C6 derivative cells expressing antisense RNA to IGF-IR RNA, C6 derivative cells expressing sense RNA to IGF-IR RNA, OF-1, and BA 11112 cell lines.

Aliquots of $5 \times 10^5$ cells were placed in diffusion chambers, that were then inserted in the subcutaneous tissue of syngeneic rats, and removed at various intervals thereafter. The number of cells in each chamber were counted, also the percentage of cells stained by trypan blue, and finally, the residual cells were plated in tissue culture dishes. Cells stably expressing the antisense RNA rapidly died in the diffusion chambers, most of the cells being dead after only 3 hours (FIG. 1), while wild type and sense cells doubled in number in 24 hours, at which time only an occasional antisense cell could still be recovered from the chambers.

Figure 2:
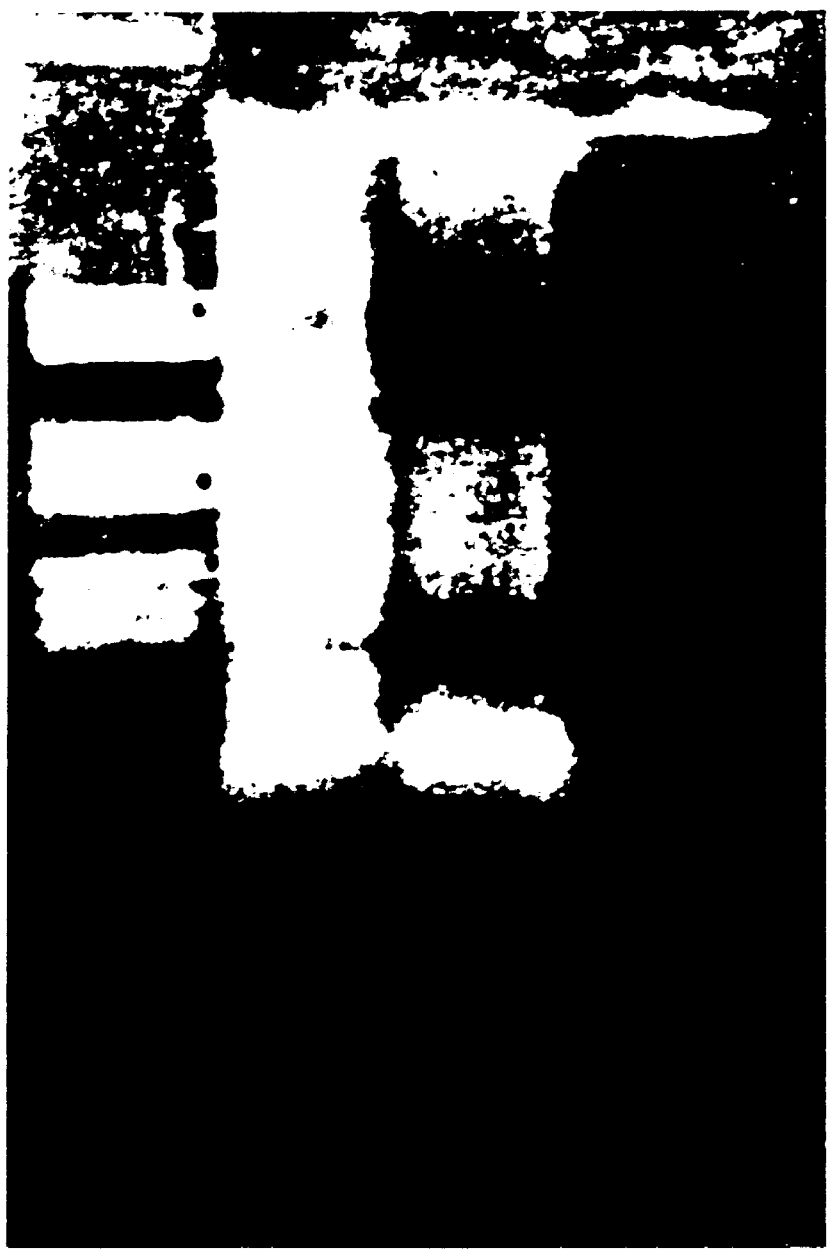
FIG. 2 shows a DNA ladder of apoptotic cells. Antisense C6 cells were placed in diffusion chambers for 40 minutes, the DNA was extracted and displayed as described in Example 1.

In one experiment, antisense C6 cells were suspended in 10% serum before placing them into a diffusion chamber; all the cells were dead by 24 hours. The antisense cells were examined for evidence of apoptosis by DNA extraction and visualization on ethidium bromide-stained gels. FIG. 2 shows the typical DNA ladder of apoptotic cells, from a sample taken 40 minutes after introduction of the antisense cells into the diffusion chambers.

When the wild type C6 cells, previously incubated with the antisense oligo, were placed in a diffusion chamber and inserted into the subcutaneous tissue of rats, the results were much more impressive, as most of the cells were dead by 24 hours (Table 2), whereas cells incubated with the control oligo doubled in number. These last two experiments indicate that the IGF-IR is even more important in vivo than in vitro, for protection from cell death.

Because cell death occurs so rapidly and because cells in a diffusion chamber are, at least in part, protected from an immune response, Lanza, et al., 1994, supra, incorporated herein by reference in its entirety, which at any rate, would not have the time to set in, other tumor cell lines were tested in the same breed of rats. The first one tested was the FO-1 human melanoma, and its two derivative cell lines, expressing either a sense or an antisense RNA to the IGF-IR. The results are summarized in Table 2; wild type human melanoma cells and sense cells doubled in 24 hours, whereas only 1% of the antisense expressing cells could be recovered after 24 hours. Other cell lines were tested, and the results are summarized also in Table 2. Note that the cell recovery is the real measure of growth and survival, since viability of the recovered cells (as determined by trypan blue) was close to 100%. These experiments show that: 1) cell death in diffusion chambers can also be achieved by pre-incubating the cells with antisense oligodeoxynucleotides to the IGF-IR RNA; and 2) that cell death in diffusion chambers can also be studied with non-syngeneic cell lines, in fact even with cells of other species. Thus, both wild type human melanoma cells, wild type rat rhabdomyosarcoma cells and murine p6 cells double in number after 24 hours in the diffusion chambers, while antisense melanoma and rhabdomyosarcoma cells and 3T3-like cells without IGF-IRs, die.

TABLE 2

Growth of Several Cell Lines in Diffusion Chambers

| cell line | percentage recovery |
|---|---|
| C6 rat glioblastoma + | 195 |
| random oligo + | 189 |
| antisense oligo + | 0 |
| etoposide | 0.025 |
| FO-1 human melanoma | |
| wild type | 200 |
| sense plasmid | 200 |
| antisense plasmid | 1.4 |

TABLE 2-continued

Growth of Several Cell Lines in Diffusion Chambers

| cell line | percentage recovery |
|---|---|
| BA 1112 rat rhabdomyosarcoma | |
| wild type | 200 |
| sense plasmid | 200 |
| antisense plasmid | 0 |
| B1792-F10 mouse melanoma | |
| wild type | 214 |
| sense plasmid | 198 |
| antisense plasmid | 0 |
| mouse melanoma B16 | |
| wild type | 214 |
| sense plasmid | 198 |
| antisense plasmid | 0.10 |
| p6 cells (3T3 overexpressing the IGF-IR) | 186 |
| T/R - (receptorless 3T3) | 0 |

The C6 rat glioblastoma cells were wild type cells treated or not with oligodeoxynucleotides (120 mg/ml, 24 hours before inoculation). In the case of etoposide (20 μg/ml), the C6 cells were pre-incubated with the drug for 16 hrs, prior to loading into the diffusion chamber, at which time viability was 100%. Human melanoma cells were wild type or stably transfected with either a sense or an antisense expression plasmid to the IGF-IR RNA. BA 1112 also consisted of the original wild type cell line, or cell lines stably transfected with either sense or antisense plasmids to the IGF-IR RNA. p6 cells are derived from Balb/c 3T3 cells, and express over $5 \times 10^5$ IGF-IRs per cell (Pietrzkowski, et al., 1992a, 1992b), incorporated herein by reference in their entirety; T/R- cells are 3T3 cells, derived from mouse embryos with a targeted disruption of the IGF-IR genes. Sell, et al., *Proc. Natl. Acad. Sci. USA*, 1993, 90, 11217–11221 and Sell, et al., *Mol. Cell. Biol.*, 1994, 14, 3604–3612, incorporated herein by reference in their entirety. The percentage changes are after 24 hours in diffusion chambers in rats.

Growth Curves $5 \times 10^4$ C6 cells were plated in 35 mm dishes in 10% serum; after 4 hours the growth medium was removed and replaced with serum-free medium, supplemented with 0.1% bovine serum albumin (fraction V) and 1 μM ferrous sulfate, with or without IGF-I (10 ng/ml). Random or antisense oligodeoxynucleotides (Lynx Therapeutics, Hayward, Calif.) were added at a concentration of 120 μg/ml, directly to the medium. The cells were counted after 24 and 48 hours, using a hemocytometer. Viability was determined by trypan blue exclusion. This procedure was repeated for C6 derivative cells expressing antisense RNA to IGF-IR RNA and C6 derivative cells expressing sense RNA to IGF-IR RNA, FO-1, and BA 11112 cell lines.

Plating of cells resulted in rapid overgrowth with the wild type and sense cells, whereas antisense cells, after 24 hours in the diffusion chambers, did not produce any colony in vitro.

Determination of Apoptosis

Cells were lysed in 50 μl of lysis buffer (10 mM EDTA, 50 mM Tris pH 8,0.5% sodium dodecyl sulfate, 0.5 mg/ml proteinase K). RNAse A (0.5 mg/ml) was added and lysates were incubated for 1 hr. at 37. Two phenol extraction (equal volumes) were performed, followed by one chloroform extraction. DNA was precipitated with two volumes of ice-cold ethanol and incubated at −80° C. for 1 hr. DNA was pelleted by centrifugation at 14,000 rpm for 10 minutes at 4° C. Pellets were air-dried for 30 minutes, resuspended in 50

μl of Tris-EDTA pH 8. DNA was electrophoresed in a 1.8% agarose gel in 1×TBE running buffer (0.05 M Tris base, 0.05 M boric acid, 1 mM disodium EDTA), according to the methods of Preston, et al., *Cancer Res.*, 1994, 54, 4214–4223, incorporated herein by reference in its entirety.

Example 2

Protective and Curative Effects Against Tumor Growth by Apoptotic Cells in Diffusion Chambers C6 cells constitutively expressing an antisense RNA to the IGF-IR RNA and C6 cells pre-treated for 24 hours with antisense oligodeoxynucleotides of SEQ ID NO: 2 (−29 to −24 of the signal sequence) to the same RNA (at a concentration of 120 μg/ml) were inoculated into diffusion chambers ($5 \times 10^5$ cells per chamber in 0.2 ml of phosphate buffered saline), which were then inserted into the subcutaneous tissue of 7-week-old male BD-IX rats (Charles River Breeders Laboratories, Boston, Mass.). Untreated C6 cells, C6 cells expressing a sense RNA, and C6 cells pre-treated with a randomly mismatched oligodeoxynucleotide at each nucleic acid position of the −29 to −24 signal sequence were used as controls. Since these 3 groups of cells behaved in exactly the same manner, they are included into a single control group.

The diffusion chambers were removed at various intervals after insertion, ranging from 15 minutes to 48 hours. Seven days later, the rats were challenged with $10^7$ wild type C6 cells, injected above the right hind leg.

The results are summarized in Table 3. The first column (cells in diffusion chamber) indicates the treatment; the second column (% recovery) reveals the number of cells recovered expressed as percentage of cells inoculated; and the 3rd column (tumor development) gives the number of rats with tumors after challenging the animals, previously carrying the diffusion chambers, with $10^7$ wild type C6 cells, subcutaneously.

TABLE 3

| cells in diffusion chambers | % recovery | tumor development |
| --- | --- | --- |
| control group | 200 | 15/15 (day 5) |
| antisense transfected 45 minutes | 65 | 9/9 (day 5) |
| antisense transfected 3 hours | 0–4 | 0/12 |
| antisense oligos 24 hours | 0 | 0/3 |

The first column indicates the times (in minutes and hours), after insertion, when the diffusion chambers were removed. The second column gives the percentage of live cells that were recovered. The third column reveals the appearance of wild type tumors after the rats that had received the diffusion chamber were challenged with C6 cells. Day 5 in the 3rd column is the latent period, after injection of wild type cells, for the appearance of a palpable tumor.

This example shows that resistance against subsequent challenge with homologous wild type tumor cells can be achieved either by placing in diffusion chambers cells transfected with a plasmid expressing an antisense RNA to the IGF-IR RNA (Resnicoff, et al., 1994a, 1994b, supra.), incorporated by reference in its entirety, or by pre-treatment of wild type cells with antisense oligonucleotides to the IGF-IR RNA. They also indicate that resistance is conferred, when some cells are still alive (diffusion chamber left in the rat for 3 hours), i.e. it is not necessary for all cells in the chamber to die to induce resistance.

Example 3

Regression of Established Tumors by Apoptotic Cells in Diffusion Chambers

The expression plasmids used, and the C6 cells and their derivatives used in these experiments have been described in detail in papers by Resnicoff, et al., 1994a, 1994b, supra.), incorporated by reference in their entirety. The oligodeoxynucleotide sequences are provided by Resnicoff, et al., the antisense was originally described in Pietrzkowski, et al. 1992a, 1992b, supra, incorporated by reference in their entirety.

$10^7$ wild type C6 cells were injected subcutaneously above the right hind leg of 7-week-old male BD-IX rats. Tumors appeared at day 5, as usual. On day 7, some animals, selected at random, received diffusion chambers containing $5 \times 10^5$ C6 cells constitutively expressing an antisense RNA to the IGF-IR RNA (Resnicoff, et al., 1994a, 1994b). After 24 hours, the diffusion chambers were removed, and no cells could be recovered from them. Five days later, the rats who received the diffusion chambers had tumors considerably smaller than the control animals (no chambers). Seven days after removal of the diffusion chambers (14 days after injection of wild type cells), the results were as follows:

TABLE 4

| condition | tumor development |
| --- | --- |
| control rats | 3/3 |
| treated rats | 0/3 |

Con0trol rats were injected with $10^7$ wild type C6 cells and did not receive a diffusion chamber; treated rats received, 7 days after injection of wild type cells, a diffusion chamber with $5 \times 10^5$ C6 cells expressing an antisense RNA of SEQ ID NO: 1, to nucleic acids positions 1 to 309 to the IGF-IR RNA of FIGS. 4A–4G. In treated rats, no residual tumor could be detected at autopsy (histological examination).

This example shows that homologous tumor cells, expressing an antisense RNA to the IGF-IR RNA, inoculated into diffusion chambers, induces regression of already well established wild type tumors.

Example 4

Induction of resistance to Tumor Cells

The extent to which the tumor cells undergoing apoptosis in the diffusion chambers protect rats from the subsequent challenge with wild type C6 cells is shown in this experiment. For this purpose, different, non-syngeneic and non-homologous types of cells were inserted as usual in diffusion chambers, for a period of 24 hours. The chambers were removed, monitored for recovery of cells, and the rats were subsequently challenged with $10^7$ wild type C6 cells, following the same protocols described above. The results are summarized in Table 5, where subsequent to challenge, (−)=no tumor, (+)=no regression.

TABLE 5

| cell type in chambers | % recovery | tumor development |
|---|---|---|
| Human melanoma cells (antisense) | 1.4 | (−) |
| BA-1112 (antisense) | 0 | (−) |
| (tsA)R− | 0 | (−) |
| Balb/c3T3 | 0.8 | (+) |
| (tsA)R+ | 3.2 | (+) |
| C6 cells + etoposide | 0.025 | (−) |

Human melanoma cells are OF-1 cells expressing an antisense RNA to the IGF-IR RNA (Resnicoff, et al. 1994a, 1994b, incorporated by reference in their entirety); BA-1112 are cells from a transplantable rat sarcoma, also expressing an antisense RNA to the IGF-IR RNA; (tsA)R−, Balb/c 3T3 and (tsA)R+ are 3T3-like mouse cells, described in detail in Sell, et al., 1994, supra., incorporated herein by reference in its entirety; C6 cells+etoposide, are wild type C6 cells pre-treated for 16 hrs with the topoisomerase inhibitor, etoposide. At the moment of loading the chamber, cells pre-treated with etoposide (20 μg/ml) were 100% viable. After 24 hrs, in vivo, only 125 cells could be recovered, of which 50% were viable, from which the percent recovery was calculated.

These experiments show that, curiously enough, when the cells placed in the diffusion chambers lacked the IGF-IR or had markedly reduced numbers, they protected rats from a subsequent challenge with wild type C6 rat glioblastoma cells, regardless of the species of cells used in the chambers. Cells with a normal number of IGF-I receptors, under the same conditions, did not display a protective effect. This seems to indicate that the protective effect of antisense strategies against the IGF-I receptor RNA cuts across species barriers.

Example 5
Induction of Tumor Resistance with Pro-Apoptotic Agents

In the following experiments, cells were cultured in vitro in the presence of the particular pro-apoptotic agent for 24 hours. The tumor cells were detached from the culture plates, washed three times with phosphate buffered saline (PBS) and resuspended in PBS prior to being placed in diffusion chambers, as described in Resnicoff, et al., *Cancer Res.*, 1995, 55, 2463–2469, incorporated herein by reference. The diffusion chambers were subsequently implanted into the subcutaneous tissue in rats or mice. Twenty four hours later, the cells were recovered from the diffusion chambers, stained with trypan blue, and counted in a hemocytometer. The results are shown in Table 6, and are given as percentage of cells undergoing apoptosis and induction of tumor resistance.

TABLE 6

| Condition | Apoptosis (%) | Induction of Tumor Resistance |
|---|---|---|
| C6 rat glioblastoma + soluble IGF-IR | 95 | YES |
| CaOV-3 human ovarian carcinoma + MyCF MHC Class I peptides ($10^{-5}$ to $10^{-8}$M) + | 99 | YES |
| ovarian carcinoma | 90 to 96.5 | YES |
| glioblastoma | 95 | YES |
| colon carcinoma | 30 | not tested |
| small cell lung carcinoma | 30 | not tested |
| melanoma | 25 | not tested |
| C6 rat glioblastoma + etoposide (20 μM/16 hours) | 99.975 | YES |
| camptothecin (5 × $10^{-9}$M/ 6 hours) | 95 | YES |
| mouse sarcoma + etoposide (20 μM/16 hours) | 98 | not tested |
| P6 mouse fibroblasts + TNF-α (10 pg/6 hours) | 99.9 | not tested |

Example 6
Testing Agents for Anti-Cancer Activity In Vivo Using Diffusion Chambers As set forth above, the present invention provides an in vivo method of screening agents for anti-cancer therapeutic activity, such as, for example, apoptosis activity. Tumor cells in media in vitro are supplemented with a test compound for a period of time between 3 hours and 48 hours, preferably 24 hours. After in vitro culture, the tumor cells are placed in a diffusion chamber, which is subsequently implanted into a test animal, such as a rat or mouse, or other suitable mammal. Alternatively, the tumor cells are cultured in the absence of a test compound. The tumor cells are transferred to a diffusion chamber which is implanted into a mammal, and the mammal is given the test compound. The test compound is evaluated for anti-cancer efficacy, i.e., apoptosis activity as described herein, and the effect of the test compound on induction of tumor resistance is also evaluated.

Tumor cells that may be used in the diffusion chamber include any cells capable of being inhibited by anti-cancer agents, i.e., undergoing apoptosis when exposed to an anti-cancer agent or pro-apoptotic agent. Such cells include, but are not limited to rat glioblastoma, human glioblastoma, human melanoma, human breast carcinoma, human lung carcinoma, mouse melanoma, mouse leukemia, human ovarian carcinoma, human rhabdomyosarcoma, rat rhabdomyosarcoma, pancreatic carcinoma cells, C6 rat glioblastoma, and the like, as well as those disclosed above. It is contemplated that any cancer cell may be used to test the anti-cancer efficacy of a test agent.

Tumor cells can be placed in a diffusion chamber in varying amounts. Preferably, about $1 \times 10^4$ to about $5 \times 10^6$ cells can be placed in the diffusion chamber. More preferably, about $10^5$ to about $1.5 \times 10^6$ cells can be placed in the diffusion chamber. Most preferably, about $5 \times 10^5$ cells are placed in the chamber. The cells are placed in the diffusion chamber containing media. It is contemplated that any media that supports the growth of cancer cells can be used.

Test agents may be administered to individuals as a single or in multiple doses. Preferred for pharmaceutical compositions that comprise the test agents in combination with a pharmaceutically acceptable carrier or diluent. The pharmaceutical compositions may be administered by any means that enables the active agent to reach the diffusion chamber in the body of animal. Agents may be administered orally, or by parenteral administration, i.e., intravenous, subcutaneous, intramuscular depending on their chemical or physical nature. In some preferred embodiments, pharmaceutical compositions which comprise the agents are administered intravenously or subcutaneously. Pharmaceutical compositions may be administered either as individual therapeutic agents or in combination with other therapeutic agents. They can be administered alone, but are generally administered with a pharmaceutical carrier selected on the basis of the chosen route of administration and standard pharmaceutical practice. The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. A test agent is placed in the in vitro tumor cell culture prior to washing the cells and placing them inside a diffusion chamber or delivered to the test animal outside the chamber at a variety of concentrations ranging from about 1 picogram to about 1 g. In some embodiments, test agents may be used at a concentration of about 1 $\mu$g to about 100 $\mu$g. Usually a daily dosage of active ingredient can be about 1 pg to 1 grams per kilogram of body weight, in some embodiments about 0.1 pg to 100 mg per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results. Dosage forms (composition) suitable for internal administration generally contain from about 1 milligram to about 500 milligrams of active ingredient per unit. In these pharmaceutical compositions the active ingredient will ordinarily be present in an amount of about 0.5–95 by weight based on the total weight of the composition.

For parenteral administration, the test compound can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of *Remington's Pharmaceutical Sciences*, A. Osol, a standard reference text in this field. For example, a parenteral composition suitable for administration by injection is prepared by dissolving 1.5% by weight of active ingredient in 0.9% sodium chloride solution.

Peptides and proteins may be delivered in protein form or provided by expression vectors or by infection through virions. One skilled in the art is readily able to deliver test agents by numerous methods widely known to those skilled in the art. Test agents may be delivered alone or in combination with other test agents.

The diffusion chamber containing tumor cells treated with or without the test agent(s) is implanted into a mammal, preferably a rat or mouse. The mammal can be tumor-free, or can be tumor-expressing. Tumor-expressing mammals include those which express tumors naturally, or those in which tumor cells are injected. The diffusion chamber is implanted subcutaneously or intraperitoneally, for example, in tumor-free or tumor-expressing mammals. The chamber may be removed about 6 to about 96 hours after implantation. Preferably, the chamber is removed about 12 to about 72 hours after implantation. More preferably, the chamber is removed about 18 to about 48 hours after implantation. Most preferably, the chamber is removed about 24 to about 30 hours after implantation. It is contemplated that a range of times will be used to establish optimum activity of the test compound. Alternatively, a refillable chamber may be employed such that the chamber may be re-used for treatments and emptied following treatments. Anti-cancer efficacy can be evaluated by determining the extent of growth inhibition or death of tumor cells in the diffusion chamber. In addition, mice or rats with naturally growing tumors or those injected with tumor cells can be implanted as described above. The effect of the test agent on tumor cells outside the diffusion chamber can be determined as described above. Apoptosis can be determined by methods such as, for example, DNA ladder, electron or light microscopy, flow cytometry, and different commercially available kits for the determination of apoptosis.

Example 7

Induction of Resistance to Melanoma

C57/BL6 mice were injected subcutaneously with $10^5$ B1792-F10 mouse melanoma cells. The cells were either untreated or pretreated for 24 hours prior to injection with either sense or antisense oligonucleotides to IGF-IR. Mice were injected a second time into the left flank. The size of the tumors at the time of the second injection was 2 to 2.5 grams. The results of this experiment are shown in Table 7.

TABLE 7

| cells injected first injection (right flank) | second injection (left flank) | tumor development number of animals (palpable tumors in days) |
|---|---|---|
| untreated | | 6/6 (4–5) dead by day 16 |
| sense | | 6/6 (5–6) dead by day 18 |
| antisense | | 0/6 (negative at day 62) |
| sense | untreated | 3/3 bilateral tumors |
| antisense | untreated | 0/3 (negative at day 55) |
| untreated | sense | 3/3 dead by day 15–16 |
| untreated | antisense | 3/3 (same tumor weight for 1 month) |

Example 8

Induction of Melanoma Tumor Resistance

C57/BL6 mice were first treated with cells placed in a diffusion chamber that was inserted into the subcutaneous tissue and removed after 24 hours. B1792-F10 mouse melanoma cells were either untreated or treated with random or antisense oligonucleotides to IGF-IR. One week after the removal of the diffusion chamber, the mice were challenged with $10^5$ untreated cells, and observed for the appearance of tumors. The results of this experiment are shown in Table 8.

TABLE 8

| condition | recovery (%) | protection against challenge with untreated cells |
|---|---|---|
| untreated | 218 | NO (tumors appeared on day 5) |
| random oligonucleotide 13 $\mu$M | 209 | NO (tumors appeared at day 5) |

TABLE 8-continued

| condition | recovery (%) | protection against challenge with untreated cells |
|---|---|---|
| antisense oligonucleotide 13 μM | 114 | partial protection (tumors appeared at day 12) |
| random oligonucleotide 19 μM | 196 | NO (tumors appeared at day 5) |
| antisense oligonucleotide 19 μM | 0.1 | YES (no tumors for greater than 1 month) |

Example 9

Induction of Resistance With MHC Class I Peptides

C6 cells were incubated with an MHC Class I associated peptide at several concentrations for 24 hours in medium before injection ($10^5$ cells in 0.1 ml) into the subcutaneous tissue of 7-week-old male Balb/c mice. Percentage recovery based on the initial inoculum was determined in parallel experiments using diffusion chambers. Diffusion chambers were removed from the animals after 24 hours and viable cell were quantified by trypan blue exclusion. The results are presented in Table 9.

TABLE 9

| Treatment | Recovery (%) | Expected delay (days) | Palpable Tumors (days) |
|---|---|---|---|
| None | 212.0 ± 2.0 | 4 | 4 |
| control peptide ($10^{-5}$M) | 208.0 ± 1.3 | 4 | 4 |
| peptide ($10^{-12}$M) | 18.0 ± 0.6 | 8 | 11 |
| peptide ($10^{-10}$M) | 4.5 ± 0.2 | 10 | 14 |
| peptide ($10^{-8}$M) | 2.1 ± 0.1 | 11 | 14 |
| peptide ($10^{-5}$M) | 0.3 ± 0.01 | 14 | 21 |

The control peptide had the amino acid sequence Tyr-Leu-Glu-Pro-Gly-Ala-Val-Thr-Ala (SEQ ID NO: 15). The peptide used in the experiments had the amino acid sequence Tyr-Leu-Arg-Pro-Gly-Pro-Val-Thr-Ala (SEQ ID NO: 16). Expected delay is the number of days after injection before the tumors should become palpable, based on survival in vivo estimated by percentage of cells recovered. The last column gives the actual number of days after injection when tumors become palpable. Three nude mice were used for each experimental condition.

In another experiment, CaOV-3 human ovarian carcinoma cells ($5 \times 10^5$ cells) were implanted in diffusion chambers in the subcutaneous tissue of mice. MHC Class I associated peptides were injected subcutaneously (0.2 ml of a $5 \times 10^5$ M solution) simultaneous and adjacent to the diffusion chambers. Three mice were used for each experimental condition. The results are shown in Table 10 below.

TABLE 10

| peptide | recovery (% at 24 hours) |
|---|---|
| peptide (SEQ ID NO: 16) | 3.0 ± 0.1 |
| peptide (SEQ ID NO: 10) | 0.2 ± 0.01 |
| peptide (SEQ ID NO: 14) | 6.6 ± 0.2 |
| control peptide (SEQ ID NO: 15) | 280.0 ± 8.4 |

Various modifications of the invention in addition to those shown and described herein will be apparent to those skilled in the art from the foregoing description. Such modifications are also intended to fall within the scope of the appended claims.

What is claimed is:

1. A method of screening a pro-apoptotic agent for anti-cancer activity in a mammal having cancer comprising the steps of:

providing an in vitro tumor cell culture supplemental with said pro-apoptotic agent;

placing said tumor cells from said tumor cell culture into a diffusion chamber, thereby producing a tumor cell-containing diffusion chamber;

inserting said tumor cell-containing diffusion chamber into said mammal for a period of time; and removing said tumor cell-containing diffusion chamber and evaluating the anti-cancer effects of said pro-apoptotic agent by determining the inhibition of growth of the tumor cells in said mammal or the presence or absence of tumors in said mammal;

wherein said tumor cell is a glioblastoma tumor cell, pancreatic tumor cell, melanoma tumor cell, prostate tumor cell, ovary tumor cell, mammary tumor cell, lung tumor cell, colon tumor cell, or smooth muscle tumor cell.

2. The method of claim 1 wherein said pro-apoptotic agent is an oligonucleotide directed against DNA or RNA of a growth factor or growth factor receptor.

3. The method of claim 1 wherein said pro-apoptotic agent is an oligonucleotide directed against DNA or RNA of insulin growth factor-1 receptor.

4. A method of screening pro-apoptotic agents for anti-cancer activity in a mammal having cancer comprising the steps of:

providing an in vitro tumor cell culture supplemented with said pro-apoptotic agent;

placing said tumor cells from said tumor cell culture into a diffusion chamber, thereby producing a tumor cell-containing diffusion chamber;

inserting said tumor cell-containing diffusion chamber into said mammal for a period of time; and removing said tumor cell-containing diffusion chamber and evaluating the anti-cancer effects of said pro-apoptotic agent by evaluating apoptosis of said tumor cells in said diffusion chamber and the presence or absence of tumors in said mammal.

5. A method of inducing resistance to tumor growth in a mammal comprising:

pretreating tumor cells in vitro with etoposide or camptothecin;

placing said pretreated tumor cells in a diffusion chamber, thereby producing a tumor cell-containing diffusion chamber, wherein said pretreated tumor cells are selected from the group consisting of glioblastoma, pancreatic, melanoma, prostate, ovary, mammary, lungs, colon, and smooth muscle; and inserting said tumor cell-containing diffusion chamber into said mammal for a therapeutically effective time, thereby inducing resistance to tumor growth.

6. The method of claim 5 wherein a therapeutically effective time is a time permitting death of said tumor cells in said cell-containing chamber and resistance of said tumor growth in said mammal.

7. The method of claim 5 wherein said pretreated tumor cells are excised from said mammal.

8. The method of claim 5 wherein said pretreated tumor cells are selected from the group consisting of autografts, allografts, syngeneic, non-syngeneic, and xenografts.

9. The method of claim 5 wherein said mammal is human.

10. A method of screening an agent for anti-cancer activity in a mammal having cancer comprising the steps of:

providing an in vitro tumor cell culture supplemented with said agent;

placing said tumor cells from said tumor cell culture into a diffusion chamber, thereby producing a tumor cell-containing diffusion chamber;

inserting said tumor cell-containing diffusion chamber into said mammal for a period of time; and removing said tumor cell-containing diffusion chamber and evaluating the anti-cancer effects of said agent by determining the inhibition of growth of the tumor cells in said mammal or the presence or absence of tumors in said mammal;.

11. The method of claim 10 wherein said agent is an oligonucleotide directed against DNA or RNA of a growth factor or growth factor receptor.

12. The method of claim 10 wherein said agent is an oligonucleotide directed against DNA or RNA of insulin growth factor-1 receptor.

* * * * *